United States Patent [19]
Coats et al.

[11] Patent Number: 5,973,119
[45] Date of Patent: Oct. 26, 1999

[54] CYCLIN E GENES AND PROTEINS

[75] Inventors: Steven Roy Coats, Camarillo; Michael Brian Bass, Thousand Oaks; Murray O. Robinson, Malibu, all of Calif.

[73] Assignee: Amgen Inc., Thousand Oaks, Calif.

[21] Appl. No.: 09/092,770

[22] Filed: Jun. 5, 1998

[51] Int. Cl.$^6$ ............................... C07I 1/00; C07H 21/04
[52] U.S. Cl. ........................................ 530/350; 536/23.5
[58] Field of Search ........................... 530/350; 536/23.5

[56] References Cited

U.S. PATENT DOCUMENTS

| | | | |
|---|---|---|---|
| 3,773,919 | 11/1973 | Boswell et al. | 424/19 |
| 4,892,538 | 1/1990 | Aebischer et al. | 604/891.1 |
| 4,970,154 | 11/1990 | Chang | 435/172.2 |
| 5,011,472 | 4/1991 | Aebischer et al. | 604/50 |
| 5,106,627 | 4/1992 | Aebischer et al. | 424/424 |
| 5,252,714 | 10/1993 | Harris et al. | 530/391.9 |
| 5,399,346 | 3/1995 | Anderson et al. | 424/93.21 |
| 5,449,755 | 9/1995 | Roberts et al. | 530/350 |
| 5,489,743 | 2/1996 | Robinson et al. | 800/2 |
| 5,557,032 | 9/1996 | Mak | 800/2 |
| 5,593,875 | 1/1997 | Wurm et al. | 435/172.3 |
| 5,631,236 | 5/1997 | Woo et al. | 514/44 |
| 5,635,399 | 6/1997 | Kriegler et al. | 435/320.1 |
| 5,645,999 | 7/1997 | Roberts et al. | 435/7.4 |
| 5,653,975 | 8/1997 | Baetge et al. | 424/93.1 |
| 5,672,344 | 9/1997 | Kelly et al. | 424/93.2 |
| 5,676,954 | 10/1997 | Brigham | 424/450 |
| 5,679,559 | 10/1997 | Kim et al. | 435/172.3 |
| 5,688,665 | 11/1997 | Massague et al. | 435/69.2 |

FOREIGN PATENT DOCUMENTS

| | | |
|---|---|---|
| 0 036 676 | 3/1979 | European Pat. Off. . |
| 0 038 481 | 4/1981 | European Pat. Off. . |
| 0 088 046 | 2/1983 | European Pat. Off. . |
| 0 143 949 | 10/1984 | European Pat. Off. . |
| 0 133 988 | 3/1985 | European Pat. Off. . |
| 0 154 316 | 3/1985 | European Pat. Off. . |
| 0 401 384 | 12/1989 | European Pat. Off. . |
| WO 91/10425 | 7/1991 | WIPO . |
| WO 93/06123 | 4/1993 | WIPO . |
| WO 94/28122 | 12/1994 | WIPO . |
| WO 96/02140 | 2/1996 | WIPO . |
| WO 96/40958 | 12/1996 | WIPO . |
| WO 98/03649 | 1/1998 | WIPO . |

OTHER PUBLICATIONS

Ausubel et al., eds., Current Protocols in Molecular Biology, Green Publishers Inc. and Wiley and Sons, NY (1994) (Table of Contents Provided).

Chevalier et al., "Xenopus cyclin E, a nuclear phosphoprotein, accumulates when oocytes gain the ability to initiate DNA replication", *J. Cell Sci.*, 109: 1173–1184 (1996).

Coats et al., "23 Cell cycle regulation", Signal Transduction, Heldin and Purton, eds., Chapman and Hall, publishers, 347–360 (1996).

Cook, "Scintillation proximity assay: a versatile high–throughput screening technology", *Drug Discovery Today*, 1: 287–294 (1996).

Damjanov et al., "Molecular Cloning and Characterization of Murine Cyclin E#", *Biochem. Biophys. Res. Comm.*, 201:994–1000 (1994).

Dayhoff et al., *Atlas of Protein Sequence and Structure*, 5, supp. 3 (1978) (Table of Contents Provided).

Diehl et al., "A Dominant–Negative Cyclin D1 Mutant Prevents Nuclear Import of Cyclin–Dependent Kinase 4 (CDK$) and Its Phosphorylation by CDK–Activating Kinase", *Mol. Cell. Biol.*, 17: 7362–7374 (1997).

Engels et al., "Gene Synthesis", *Angew. Chem. Intl. Ed.*, 28: 716–734 (1989).

Eppstein et al., "Biological activity of liposome–encapsulated murine interferon is mediated by a cell membrane receptor", *Proc. Natl. Acad. Sci. USA* 82: 3688–3692 (1985).

Francis, "Protein modification and fusion proteins", *Focus on Growth Factors*, 3: 4–10 (1992).

Genbank Accession No. R84331.

Gennaro, ed., *Remington's Pharmaceutical Sciences*, 18$^{th}$ Edition, Mack Publishing Company (1990) (Table of Contents Provided).

Gray–Bablin et al., "Cyclin E, a redundant cyclin in breast cancer", *Proc. Natl. Acad. Aci USA*, 93: 15215–15220 (1996).

Gudas et al., "Nuclear posttranscriptional processing of thymidine kinase mRNA at the onset of DNA synthesis", *Proc. Natl. Acad. Sci. USA*, 85: 4705–4709 (1988).

Harlow et al., eds., Cold Spring Harbor Laboratory Press, Cold Spring Harbor, NY p. 49 (1998).

Houghten et al., "General method for the rapid solid–phase synthesis of large numbers of peptides: Specificity of antigen–antibody interaction at the level of individual amino acids", *Proc Natl Acad. Sci. USA*, 82: 5131 (1985).

Kitts et al., "A Method for Producing Recombinant Baculovirus Expression Vectors at High Frequency", *Biotechniques*, 14:810–817 (1993).

Koff et al., "Human Cyclin E, a New Cyclin That Interacts with Two Members of the CDC2 Gene Family", *Cell*, 66: 1217–1228 (1991).

Langer et al., "Biocompatibility of polymeric delivery systems for macromolecules", *J. Biomed. Mater. Res.*, 15: 267–277 (1981).

Langer, "Controlled release of macromolecules", *Chem. Tech.*, 12: 98–105 (1982).

Lauper et al., "A New G1–Specific Cyclin in Mammalian Cells", *Abstracts from the 1998 Cold Spring Harbor Laboratory Cell Cycle Meeting*, Cold Spring Harbor Laboratory Press, Cold Spring Harbor, NY, p. 115 (1998).

Lees, "Cyclin dependent kinase regulation", *Curr. Opinions Cell Biol.*, 7: 773–780 (1995).

(List continued on next page.)

*Primary Examiner*—Karen Cochrane Carlson
*Assistant Examiner*—Maryam Monshipouri
*Attorney, Agent, or Firm*—Nancy A. Oleski; Ron K. Levy; Steven M. Odre

[57] ABSTRACT

Disclosed are nucleic acid molecules encoding novel cyclin E2 polypeptides. Also disclosed are methods of preparing the nucleic acid molecules and polypeptides, and methods of using these molecules.

5 Claims, 15 Drawing Sheets

OTHER PUBLICATIONS

Lucklow et al., "Efficient Generation of Infectious Recombinant Baculoviruses by Site–Specific Transposon–Mediated Insertion of Foreign Genes into a Baculovirus Genome Propagated in *Escherichia coli*", *J. Virol.*, 67: 4566–4579 (1993).

Lucklow, "Baculovirus systems for the expression of human gene products", *Curr. Opin. Biotechnol.*, 4: 564–572 (1993).

Fiona et al., "Solubilization of Protein Aggregates", *Meth. Enz.*, 182: 264–275 (1990).

Merrifield et al., "Solid Phase Peptide Synthesis. I. The Synthesis of a Tetrapeptide", *J. Am. Chem. Soc.*, 85: 2149 (1963).

Mumberg et al., "Cyclin $E_T$, a new splice variant of human cyclin E with a unique expression pattern during cell cycle progression and differentiation", *Nuc. Acids Res.*, 25: 2098–2105 (1997).

Ninomiya–Tsuji et al., "Cloning of a human cDNA encoding a CDC2–related kinase by complementation of a budding yeast cdc28 mutation", *Proc. Natl. Acad. Sci. USA*, 88: 9006–9010 (1991).

O'Reilly et al., "Endostatin: An Endogenous inhibitor of Angiogenesis and Tumor Growth", *Cell*, 88: 277–285 (1997).

Ohtsubo et al., "Human Cyclin E, a Nuclear Protein Essential for the $G_1$–to–S Phase Transition", *Mol. Cell. Biol.*, 15: 2612–2624 (1995).

Polyak et al., "Cloning of $p27^{Kip1}$, a Cyclin–Dependent Kinase Inhibitor and a Potential Mediator of Extracellular Antimitogenic Signals", *Cell*, 78: 59–66 (1994).

Porter et al., "Expression of cell–cycle regulators $p27^{Kip1}$ and cyclin E, alone and in combination, correlate with survival in young breast cancer patients", *Nature Med.*, 3: 222–225 (1997).

Prosite Accession No. PS00292.

Richardson et al., "A Drosophila $G_1$–specific cyclin E homolog exhibits different modes of expression during embryogenesis", *Development*, 119: 673–690 (1993).

Sambrook et al., *Molecular Cloning*: A Laboratory Manual, Cold Spring Harbor Laboratory Press, Cold Spring Harbor, NY (1989) (Table of Contents Provided).

Sarcevic et al., "Differential Phosphorylation of T–47D Human Breast Cancer Cell Substrates by D1–, E–, and A–type Cyclin–CDK Complexes*", *J. Biol. Chem.*, 272: 33327–33337 (1997).

Sheaff et al., "Cyclin E–CDK2 is a regulator of $p27^{Kip1}$", *Genes and Devel.*, 11: 1464–1478 (1997).

Sherr et al., "Inhibitors of mammalian $G_1$ cyclin–dependent kinases", *Genes and Devel.*, 9: 1149–1163 (1995).

Sherr, "Cancer Cell Cycles", *Science*, 274: 1672–1677 (1996).

Sidman et al., "Controlled Release of Macromolecules and Pharmaceuticals from Synthetic Polypeptides Based on Glutamic Acid", *Biopolymers*, 22: 547–556 (1983).

Stewart and Young, Solid Phase Peptide Synthesis, Pierce Chemical Co., Rockford, IL (1994) (Table of Contents Provided).

Tsai et al., "Isolation of the human cdk2 gene that encodes the cyclin A–and adenovirus E1A–associated p33 kinase", *Nature*, 353: 174–177 (1991).

Turner et al., "Expression of achaete–scute homolog 3 in Xenopus embryos converts ectodermal cells to a neural fate", *Genes and Devel.*, 8: 1434–1447 (1994).

Yarden et al., *Devel. Dynam.* 206: 1–11 (1996).

Zariwala et al., "Human Cyclin E2 Represents a Novel E–type Cyclin", *Pathways to Cancer*, p. 49 Cold Spring Harbor Winter Conference.

FIG. 1

```
ATGTCAAGAC GAAGTAGCCG TTTACAAGCT AAGCAGCAGC CCCAGCCCAG
CCAGACGGAA TCCCCCCAAG AAGCCCAGAT AATCCAGGCC AAGAAGAGGA
AAACTACCCA GGATGTCAAA AAAGAAGAG AGGAGGTCAC CAAGAAACAT
CAGTATGAAA TTAGGAATTG TTGGCCACCT GTATTATCTG GGGGGATCAG
TCCTTGCATT ATCATTGAAA CACCTCACAA AGAAATAGGA ACAAGTGATT
TCTCCAGATT TACAAATTAC AGATTTAAAA ATCTTTTTAT TAATCCTTCA
CCTTTGCCTG ATTTAAGCTG GGGATGTTCA AAAGAAGTCT GGCTAAACAT
GTTAAAAAAG GAGAGCAGAT ATGTTCATGA CAAACATTTT GAAGTTCTGC
ATTCTGACTT GGAACCACAG ATGAGGTCCA TACTTCTAGA CTGGCTTTTA
GAGGTATGTG AAGTATACAC ACTTCATAGG GAAACATTTT ATCTTGCACA
AGACTTTTTT GATAGATTTA TGTTGACACA AAAGGATATA AATAAAAATA
TGCTTCAACT CATTGGAATT ACCTCATTAT TCATTGCTTC CAAACTTGAG
GAAATCTATG CTCCTAAACT CCAAGAGTTT GCTTACGTCA CTGATGGTGC
TTGCAGTGAA GAGGATATCT TAAGGATGGA ACTCATTATA TTAAAGGCTT
TAAAATGGGA ACTTTGTCCT GTAACAATCA TCTCCTGGCT AAATCTCTTT
CTCCAAGTTG ATGCTCTTAA AGATGCTCCT AAAGTTCTTC TACCTCAGTA
TTCTCAGGAA ACATTCATTC AAATAGCTCA GCTTTTAGAT CTGTGTATTC
TAGCCATTGA TTCATTAGAG TTCCAGTACA GAATACTGAC TGCTGCTGCC
TTGTGCCATT TTACCTCCAT TGAAGTGGTT AAGAAAGCCT CAGGTTTGGA
GTGGGACAGT ATTTCAGAAT GTGTAGATTG GATGGTACCT TTTGTCAATG
TAGTAAAAAG TACTAGTCCA GTGAAGCTGA AGACTTTTAA GAAGATTCCT
ATGGAAGACA GACATAATAT CCAGACACAT ACAAACTATT TGGCTATGCT
GGAGGAAGTA AATTACATAA ACACCTTCAG AAAAGGGGGA CAGTTGTCAC
CAGTGTGCAA TGGAGGCATT ATGACACCAC CGAAGAGCAC TGAAAAACCA
CCAGGAAAAC ACTAA
```

FIG. 2

```
ATGTCAAGAC GCAGCCGTTT ACAAGCTAAG CAACATGCCC AGCCCAACCA
GCCAGACTCT CCGCAAGAAA CCCAGATAAT TCAGGCCAAG AAGAGAAAAA
CAGCACAGGA TGTCAAAAAA AGAAAGAGG AGATCACCAA GAAGCATCAG
TATGAGATTA GGAATTGTTG GCCACCTGTA CTGTCTGGAG GAATCAGCCC
TTGCATTATC ATTGAAACAC CCCATAAAGA AATAGGAACA AGTGACTTCT
CTAGATTTAC AAATTACAGA TTTAAAAATC TTTTTATTAA TCCCTCACCT
CTGCCAGATT TAAGCTGGGC ATGTTCACAG GAGGTTTGGC AAAACATGTT
ACAAAAGGAA AACAGATACG TGCATGACAA ACATTTTCAA GTTCTGCATT
CTGACCTGGA ACCACAGATG AGGTCAATAC TTTTAGACTG GCTTTTAGAG
GTTTGTGAAG TATACACTCT TCATAGGGAG ACATTTTACC TTGCCCAAGA
CTTTTTTGAC AGATTTATGT TGACACAAAA GGATGTAAAT AAAAATATGC
TTCAACTCAT TGGGATTACC TCATTGTTCA TTGCTTCCAA ACTTGAGGAA
ATCTACGCTC CTAAACTCCA AGAGTTTGCT TACGTCACTG ATGGTGCTTG
CAGTGAAGTA GATATCTTAA AGATGGAACT CAATATATTA AAGGCTTTAA
AATGGGAACT TTGTCCAGTA ACAGTCATCT CCTGGTTGAA TCTTTTTCTT
CAAGTTGATG CTGTTAAAGA TGTTCCTAAG GTTCTTCTAC CTCAATATTC
TCAGGAGACG TTCATCCAGA TAGCTCAGCT TTTAGATCTG TGCATTCTAG
CCATCGACTC TTTAGAATTT CAATACAGAA TTCTGGCTGC TGCCGCCTTA
TGTCATTTTA CCTCCATTGA AGTGGTTAAG AAAGCTTCAG GTTTGGAATG
GGATGACATC TCGGAATGTG TAGACTGGAT GGTGCCTTTT GTTAGTGTTG
TAAAAGTGT GAGTCCAGTG AAGCTGAAGA CTTTTAAGAA GATACCCATG
GAAGATAGAC ACAATATCCA GACACACACA AATTATTTGG CTTTGCTGAA
TGAAGTAAAC TATGTGAACA TCTACAGAAA AGGAGGGCAG CTGTCACCAG
TGTGTAATGG AGGCATTATG ACACCACCAA AGAGTACTGA AAAACCACCA
GGAAAACACT GA
```

FIG.3

```
  1  MSRRSSRLQA KQQPQPSQTE SPQEAQIIQA KKRKTTQDVK KRREEVTKKH
 51  QYEIRNCWPP VLSGGISPCI IIETPHKEIG TSDFSRFTNY RFKNLFINPS
101  PLPDLSWGCS KEVWLNMLKK ESRYVHDKHF EVLHSDLEPQ MRSILLDWLL
151  EVCEVYTLHR ETFYLAQDFF AYVTDGACSE DRFMLTQKDI NKNMLQLIGI TSLFIASKLE
201  EIYAPKLQEF AYVTDGACSE EDILRMELII LKALKWELCP VTIISWLNLF
251  LQVDALKDAP KVLLPQYSQE TFIQIAQLLD LCILAIDSLE FQYRILTAAA
301  LCHFTSIEVV KKASGLEWDS ISECVDWMVP FVNVVKSTSP VKLKTFKKIP
351  MEDRHNIQTH TNYLAMLEEV NYINTFRKGG QLSPVCNGGI MTPPKSTEKP
401  PGKH
```

FIG. 4

```
  1  MSRRSRLQAK  QHAQPNQPDS  PQETQIIQAK  KRKTAQDVKK  RKEEITKKHQ
 51  YEIRNCWPPV  LSGGISPCII  IETPHKEIGT  SDFSRFTNYR  FKNLFINPSP
101  LPDLSWACSQ  EVWQNMLQKE  NRYVHDKHFQ  VLHSDLEPQM  RSILLDWLLE
151  VCEVYTLHRE  TFYLAQDFFD  RFMLTQKDVN  KNMLQLIGIT  SLFIASKLEE
201  IYAPKLQEFA  YVTDGACSEV  DILKMELNIL  KALKWELCPV  TVISWLNLFL
251  QVDAVKDVPK  VLLPQYSQET  FIQIAQLLDL  CILAIDSLEF  QYRILAAAAL
301  CHFTSIEVVK  KASGLEWDDI  SECVDWMVPF  VSVVKSVSPV  KLKTFKKIPM
351  EDRHNIQTHT  NYLALLNEVN  YVNIYRKGGQ  LSPVCNGGIM  TPPKSTEKPP
401  GKH
```

FIG.5

```
ATGTCAAGAC GAAGTAGCCG TTTACAAGCT AAGCAGCAGC CCCAGCCCAG
CCAGACGGAA TCCCCCCAAG AAGCCCAGAT AATCCAGGCC AAGAAGAGGA
AAACTACCCA GGATGTCAAA AAAAGAAGAG AGGAGGTCAC CAAGAAACAT
CAGTATGAAA TTAGGAATTG TTGGCCACCT GTATTATCTG GGGGATCAG
TCCTTGCATT ATCATTGAAA CACCTCACAA AGAAATAGGA ACAAGTGATT
TCTCCAGATT TACAAATTAC AGATTTAAAA ATCTTTTTAT TAATCCTTCA
CCTTTGCCTG ATTTAAGCTG GGGATGTTCA AAAGAAGTCT GGCTAAACAT
GTTAAAAAAG GAGAGCAGAT ATGTTCATGA CAAACATTTT GAAGTTCTGC
ATTCTGACTT GGAACCACAG ATGAGGTCCA TACTTCTAGA CTGGCTTTTA
GAGGTATGTG AAGTATACAC ACTTCATAGG GAAACATTTT ATCTTGCTTA
CGTCACTGAT GGTGCTTGCA GTGAAGAGGA TATCTTAAGG ATGGAACTCA
TTATATTAAA GGCTTTAAAA TGGGAACTTT GTCCTGTAAC AATCATCTCC
TGGCTAAATC TCTTTCTCCA AGTTGATGCT CTTAAAGATG CTCCTAAAGT
TCTTCTACCT CAGTATTCTC AGGAAACATT CATTCAAATA GCTCAGCTTT
TAGATCTGTG TATTCTAGCC ATTGATTCAT TAGAGTTCCA GTACAGAATA
CTGACTGCTG CTGCCTTGTG CCATTTTACC TCCATTGAAG TGGTTAAGAA
AGCCTCAGGT TTGGAGTGGG ACAGTATTTC AGAATGTGTA GATTGGATGG
TACCTTTTGT CAATGTAGTA AAAAGTACTA GTCCAGTGAA GCTGAAGACT
TTTAAGAAGA TTCCTATGGA AGACAGACAT AATATCCAGA CACATACAAA
CTATTTGGCT ATGCTGGAGG AAGTAAATTA CATAAACACC TTCAGAAAAG
GGGACAGTT GTCACCAGTG TGCAATGGAG GCATTATGAC ACCACCGAAG
AGCACTGAAA AACCACCAGG AAAACACTAA
```

FIG. 6

```
  1  MSRRSSRLQA KQQPQPSQTE SPQEAQIIQA KKRKTTQDVK KRREEVTKKH
 51  QYEIRNCWPP VLSGGISPCI IIETPHKEIG TSDFSRFTNY RFKNLFINPS
101  PLPDLSWGCS KEVWLNMLKK ESRYVHDKHF EVLHSDLEPQ MRSILLDWLL
151  EVCEVYTLHR ETFYLAYVTD GACSEEDILR MELIILKALK WELCPVTIIS
201  WLNLFLQVDA LKDAPKVLLP QYSQETFIQI AQLLDLCILA IDSLEFQYRI
251  LTAAALCHFT SIEVVKKASG LEWDSISECV DWMVPFVNVV KSTSPVKLKT
301  FKKIPMEDRH NIQTHTNYLA MLEEVNYINT FRKGGQLSPV CNGGIMTPPK
351  STEKPPGKH
```

FIG. 7

```
   1  AUGUCCCGUC GUUCCUCCCG UCUGCAGGCU AAACAGCAGC CGCAGCCGUC
  51  CCAGACCGAA UCCCCGCAGG AAGCUCAGAU CAUCCAGGCU AAAAAACGUA
 101  AAACCACCCA GGACGUUAAA AAACGUCGUG AAGAAGUUAC CAAAAAACAC
 151  CAGUACGAAA UCCGUAACUG CUGGCCGCCG GUUCUGUCCG GUGGUAUCUC
 201  CCCGUGCAUC AUCAUCGAAA CCCCGCACAA AGAAAUCGGU ACCUCCGACU
 251  UCUCCCGUUU CACCAACUAC CGUUUCAAAA ACCUGUUCAU CAACCCGUCC
 301  CCGCUGCCGG ACCUGUCCUG GGGUUGCUCC AAAGAAGUUU GGCUGAACAU
 351  GCUGAAAAAA GAAUCCCGUU ACGUUCACGA CAAACACUUC GAAGUUCUGC
 401  ACUCCGACCU GGAACCGCAG AUGCGUUCCA UCCUGCUGGA CUGGCUGCUG
 451  GAAGUUGCG AAGUUUACAC CCUGCACCGU GAAACCUUCU ACCUGGCUCA
 501  GGACUUCUUC GACCGUUUCA UGCUGACCCA GAAAGACAUC AACAAAAACA
 551  UGCUGCAGCU GAUCGGUAUC ACCUCCCUGU UCAUCGCUUC CAAACUGGAA
 601  GAAAUCUACG CUCCGAAACU GCAGGAAUUC GCUUACGUUA CCGACGGUGC
 651  UUGCUCCGAA GAAGACAUCC UGCGUAUGGA ACUGAUCAUC CUGAAAGCUC
 701  UGAAAUGGGA ACUGUGCCCG GUUACCAUCA UCUCCUGGCU GAACCUGUUC
 751  CUGCAGGUUG ACGCUCUGAA AGACGCUCCG AAAGUUCUGC UGCCGCAGUA
 801  CUCCCAGGAA ACCUUCAUCC AGAUCGCUCA GCUGCUGGAC CUGUGCAUCC
 851  UGGCUAUCGA CUCCCUGGAA UUCCAGUACC GUAUCCUGAC CGCUGCUGCU
 901  CUGUGCCACU UCACCUCCAU CGAAGUUGUU AAAAAAGCUU CCGGUCUGGA
 951  AUGGGACUCC AUCUCCGAAU GCGUUGACUG GAUGGUUCCG UUCGUUAACG
1001  UUGUUAAAUC CACCUCCCCG GUUAAACUGA AAACCUUCAA AAAAAUCCCG
1051  AUGGAAGACC GUCACAACAU CCAGACCCAC ACCAACUACC UGGCUAUGCU
1101  GGAAGAAGUU AACUACAUCA ACACCUUCCG UAAAGGUGGU CAGCUGUCCC
1151  CGGUUUGCAA CGGUGGUAUC AUGACCCCGC CGAAUCCAC CGAAAAACCG
1201  CCGGGUAAAC ACUG
```

FIG.8

```
   1  AUGUCCCGUC GUUCCCGUCU GCAGGCUAAA CAGCACGCUC AGCCGAACCA
  51  GCCGGACUCC CCGCAGGAAA CCCAGAUCAU CCAGGCUAAA AAACGUAAAA
 101  CCGCUCAGGA CGUUAAAAAA CGUAAAGAAG AAAUCACCAA AAAACACCAG
 151  UACGAAAUCC GUAACUGCUG GCCGCCGGUU CUGUCCGGUG UAUCUCCCC
 201  GUGCAUCAUC AUCGAAACCC CGCACAAAGA AAUCGGUACC UCCGACUUCU
 251  CCCGUUUCAC CAACUACCGU UUCAAAAACC UGUUCAUCAA CCCGUCCCCG
 301  CUGCCGGACC UGUCCUGGGC UUGCUCCCAG GAAGUUUGGC AGAACAUGCU
 351  GCAGAAAGAA AACCGUUACG UUCACGACAA ACACUUCCAG GUUCUGCACU
 401  CCGACCUGGA ACCGCAGAUG CGUUCCAUCC UGCUGGACUG GCUGCUGGAA
 451  GUUUGCGAAG UUUACACCCU GCACCGUGAA ACCUUCUACC UGGCUCAGGA
 501  CUUCUUCGAC CGUUUCAUGC UGACCCAGAA AGACGUUAAC AAAAACAUGC
 551  UGCAGCUGAU CGGUAUCACC UCCCUGUUCA UCGCUUCCAA ACUGGAAGAA
 601  AUCUACGCUC CGAAACUGCA GGAAUUCGCU UACGUUACCG ACGGUGCUUG
 651  CUCCGAAGUU GACAUCCUGA AAUGGAACU GAACAUCCUG AAAGCUCUGA
 701  AAUGGGAACU GUGCCCGGUU ACCGUUAUCU CCUGGCUGAA CCUGUUCCUG
 751  CAGGUUGACG CUGUUAAAGA CGUUCCGAAA GUUCUGCUGC CGCAGUACUC
 801  CCAGGAAACC UUCAUCCAGA UCGCUCAGCU GCUGGACCUG UGCAUCCUGG
 851  CUAUCGACUC CCUGGAAUUC CAGUACCGUA UCCUGGCUGC UGCUGCUCUG
 901  UGCCACUUCA CCUCCAUCGA AGUUGUUAAA AAAGCUUCCG GUCUGGAAUG
 951  GGACGACAUC UCCGAAUGCG UUGACUGGAU GGUUCCGUUC GUUUCCGUUG
1001  UUAAAUCCGU UUCCCCGGUU AAACUGAAAA CCUUCAAAAA AAUCCCGAUG
1051  GAAGACCGUC ACAACAUCCA GACCCACACC AACUACCUGG CUCUGCUGAA
1101  CGAAGUUAAC UACGUUAACA UCUACCGUAA AGGUGGUCAG CUGUCCCCGG
1151  UUUGCAACGG UGGUAUCAUG ACCCCGCCGA AAUCCACCGA AAAACCGCCG
1201  GGUAAACACU GA
```

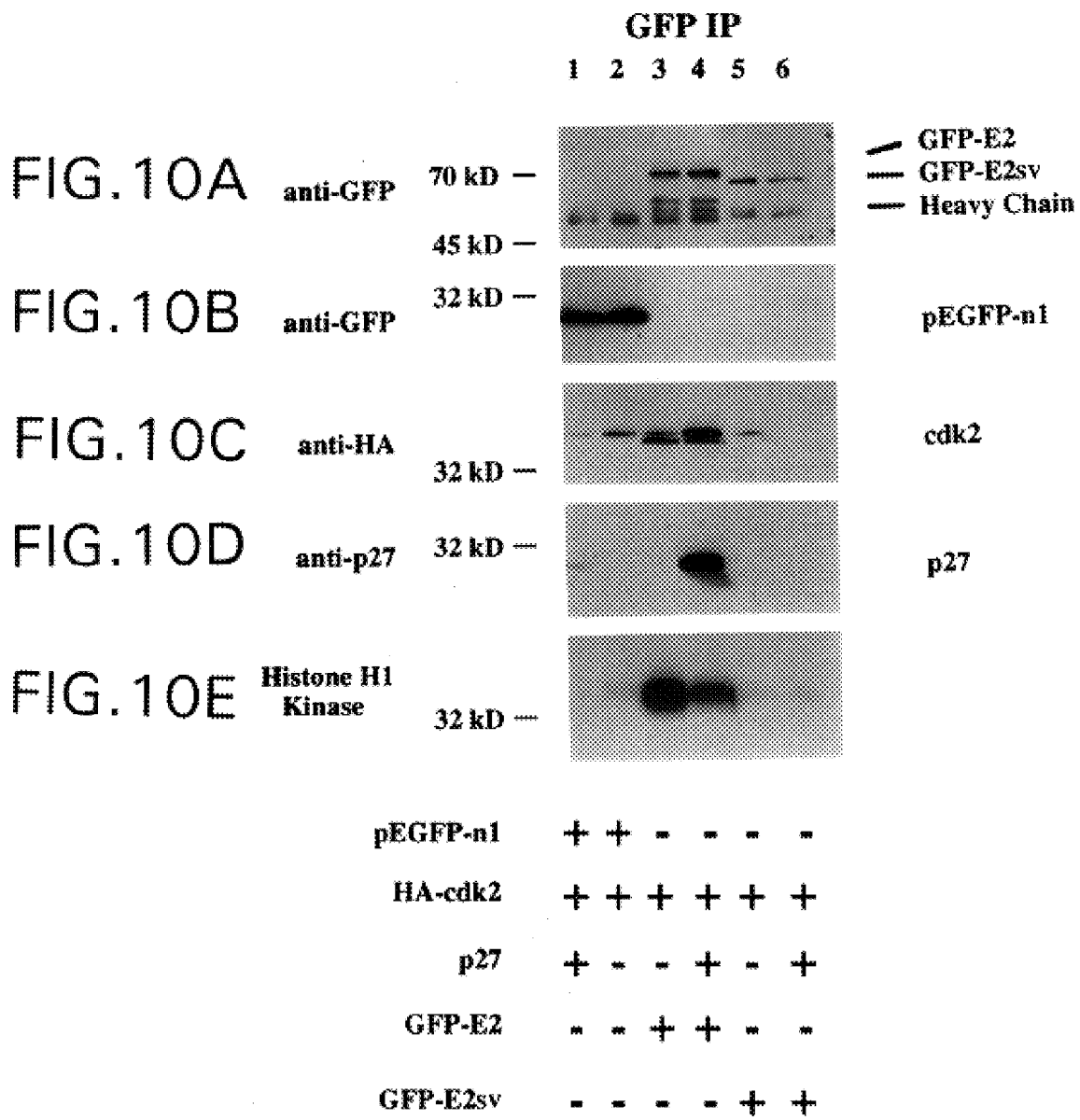

FIG. 11

ATGWSNMGNM GNWSNWSNMG NYTNCARGCN AARCARCARC CNCARCCNWS
NCARACNGAR WSNCCNCARG ARGCNCARAT HATHCARGCN AARAARMGNA
ARACNACNCA RGAYGTNAAR AARMGNMGNG ARGARGTNAC NAARAARCAY
CARTAYGARA THMGNAAYTG YTGGCCNCCN GTNYTNWSNG GNGGNATHWS
NCCNTGYATH ATHATHGARA CNCCNCAYAA RGARATHGGN ACNWSNGAYT
TYWSNMGNTT YACNAAYTAY MGNTTYAARA AYYTNTTYAT HAAYCCNWSN
CCNYTNCCNG AYYTNWSNTG GGGNTGYWSN AARGARGTNT GGYTNAAYAT
GYTNAARAAR GARWSNMGNT AYGTNCAYGA YAARCAYTTY GARGTNYTNC
AYWSNGAYYT NGARCCNCAR ATGMGNWSNA THYTNYTNGA YTGGYTNYTN
GARGTNTGYG ARGTNTAYAC NYTNCAYMGN GARACNTTYT AYYTNGCNCA
RGAYTTYTTY GAYMGNTTYA TGYTNACNCA RAARGAYATH AAYAARAAYA
TGYTNCARYT NATHGGNATH ACNWSNYTNT TYATHGCNWS NAARYTNGAR
GARATHTAYG CNCCNAARYT NCARGARTTY GCNTAYGTNA CNGAYGGNGC
NTGYWSNGAR GARGAYATHY TNMGNATGGA RYTNATHATH YTNAARGCNY
TNAARTGGGA RYTNTGYCCN GTNACNATHA THWSNTGGYT NAAYYTNTTY
YTNCARGTNG AYGCNYTNAA RGAYGCNCCN AARGTNYTNY TNCCNCARTA
YWSNCARGAR ACNTTYATHC ARATHGCNCA RYTNYTNGAY YTNTGYATHY
TNGCNATHGA YWSNYTNGAR TTYCARTAYM GNATHYTNAC NGCNGCNGCN
YTNTGYCAYT TYACNWSNAT HGARGTNGTN AARAARGCNW SNGGNYTNGA
RTGGGAYWSN ATHWSNGART GYGTNGAYTG GATGGTNCCN TTYGTNAAYG
TNGTNAARWS NACNWSNCCN GTNAARYTNA ARACNTTYAA RAARATHCCN
ATGGARGAYM GNCAYAAYAT HCARACNCAY ACNAAYTAYY TNGCNATGYT
NGARGARGTN AAYTAYATHA AYACNTTYMG NAARGGNGGN CARYTNWSNC
CNGTNTGYAA YGGNGGNATH ATGACNCCNC CNAARWSNAC NGARAARCCN
CCNGGNAARC AYTRR

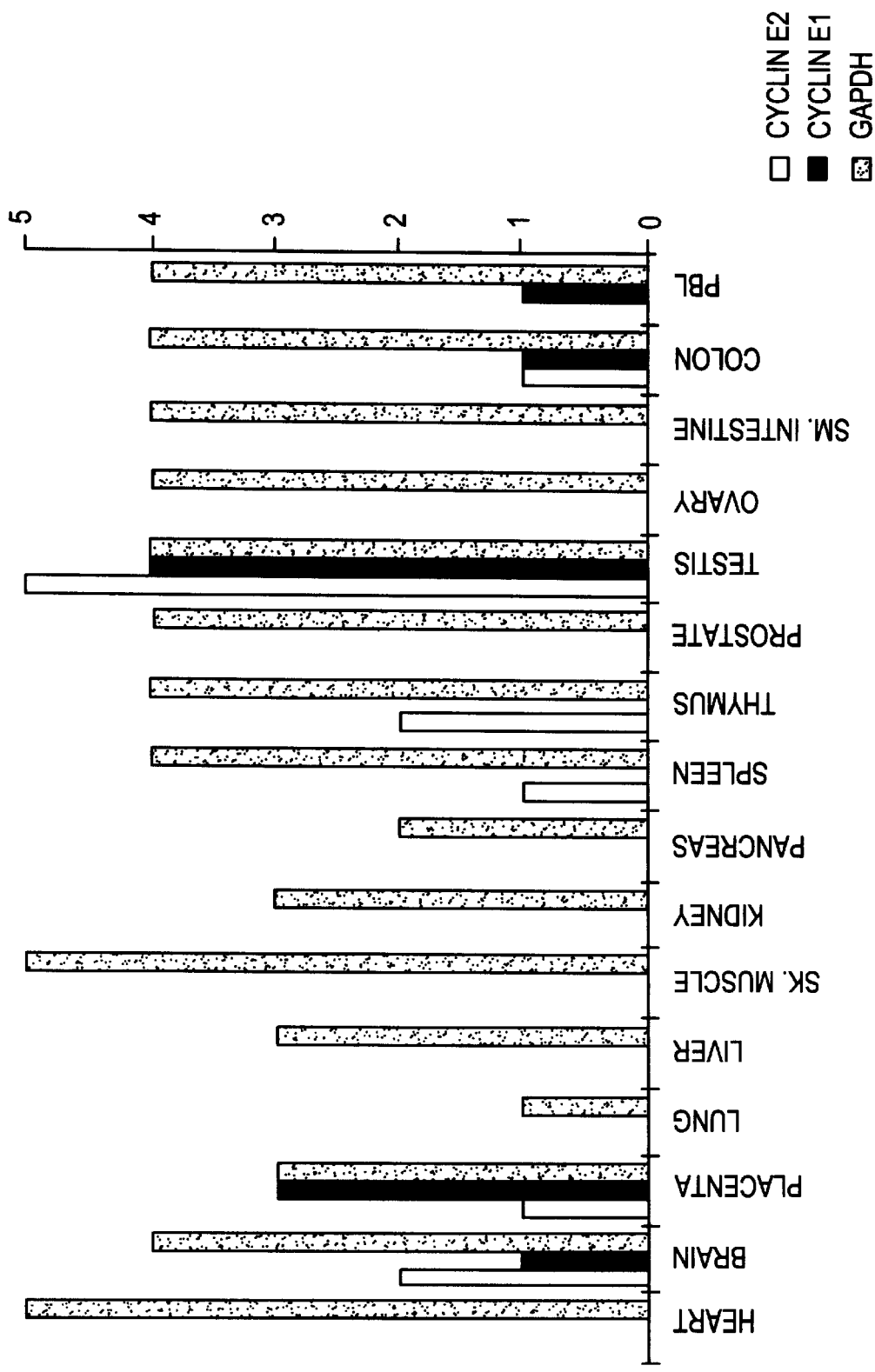

FIG. 13
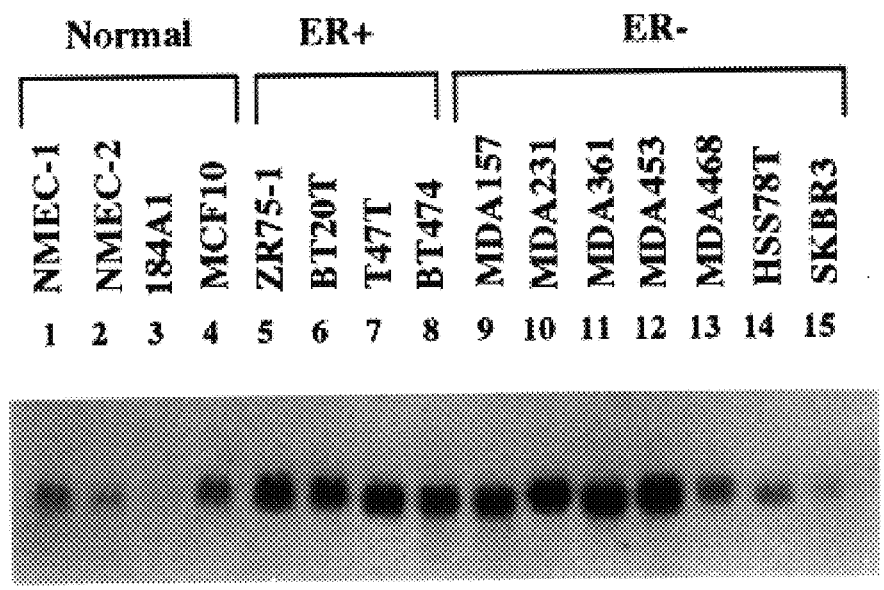
Cyclin E2
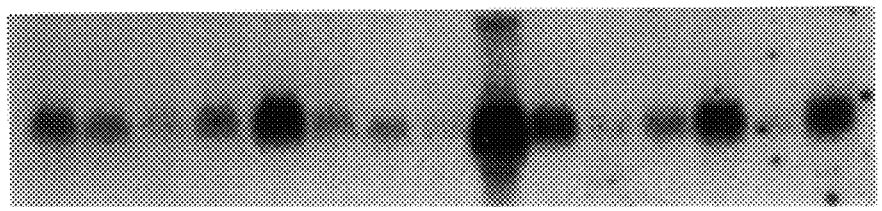
Cyclin E1

FIG. 14

ATGWSNMGNM GNWSNMGNYT NCARGCNAAR CARCAYGCNC ARCCNAAYCA
RCCNGAYWSN CCNCARGARA CNCARATHAT HCARGCNAAR AARMGNAARA
CNGCNCARGA YGTNAARAAR MGNAARGARG ARATHACNAA RAARCAYCAR
TAYGARATHM GNAAYTGYTG GCCNCCNGTN YTNWSNGGNG GNATHWSNCC
NTGYATHATH ATHGARACNC CNCAYAARGA RATHGGNACN WSNGAYTTYW
SNMGNTTYAC NAAYTAYMGN TTYAARAAYY TNTTYATHAA YCCNWSNCCN
YTNCCNGAYY TNWSNTGGGC NTGYWSNCAR GARGTNTGGC ARAAYATGYT
NCARAARGAR AAYMGNTAYG TNCAYGAYAA RCAYTTYCAR GTNYTNCAYW
SNGAYYTNGA RCCNCARATG MGNWSNATHY TNYTNGAYTG GYTNYTNGAR
GTNTGYGARG TNTAYACNYT NCAYMGNGAR ACNTTYTAYY TNGCNCARGA
YTTYTTYGAY MGNTTYATGY TNACNCARAA RGAYGTNAAY AARAAYATGY
TNCARYTNAT HGGNATHACN WSNYTNTTYA THGCNWSNAA RYTNGARGAR
ATHTAYGCNC CNAARYTNCA RGARTTYGCN TAYGTNACNG AYGGNGCNTG
YWSNGARGTN GAYATHYTNA ARATGGARYT NAAYATHYTN AARGCNYTNA
ARTGGGARYT NTGYCCNGTN ACNGTNATHW SNTGGYTNAA YYTNTTYYTN
CARGTNGAYG CNGTNAARGA YGTNCCNAAR GTNYTNYTNC CNCARTAYWS
NCARGARACN TTYATHCARA THGCNCARYT NYTNGAYYTN TGYATHYTNG
CNATHGAYWS NYTNGARTTY CARTAYMGNA THYTNGCNGC NGCNGCNYTN
TGYCAYTTYA CNWSNATHGA RGTNGTNAAR AARGCNWSNG GNYTNGARTG
GGAYGAYATH WSNGARTGYG TNGAYTGGAT GGTNCCNTTY GTNWSNGTNG
TNAARWSNGT NWSNCCNGTN AARYTNAARA CNTTYAARAA RATHCCNATG
GARGAYMGNC AYAAYATHCA RACNCAYACN AAYTAYYTNG CNYTNYTNAA
YGARGTNAAY TAYGTNAAYA THTAYMGNAA RGGNGGNCAR YTNWSNCCNG
TNTGYAAYGG NGGNATHATG ACNCCNCCNA ARWSNACNGA RAARCCNCCN
GGNAARCAYT RR

CYCLIN E GENES AND PROTEINS

FIELD OF THE INVENTION

This invention relates generally to novel genes encoding proteins that are members of the cell cycle protein family known as "cyclins". More specifically, the invention is directed to a novel protein called cyclin E2, DNA encoding cyclin E2, and methods of making and using the cyclin E2 genes and polypeptides.

BACKGROUND

Related Art
A. CDK-Cyclin Complexes

Cell division is a complex process that is regulated by a number of cellular and environmental factors. Recent studies have identified two classes of proteins that appear to play key roles in controlling the cell cycle. These classes include the cyclin-dependent protein kinases ("cdks") and the cyclins. Cdks function by phosphorylating selected protein substrates in the cell; these phosphorylated proteins in turn "signal" the cell to either enter or continue the process of cell division. For cdks to be active, i.e., to phosphorylate other proteins, they must be bound to a cyclin protein. Thus, cyclins "regulate" the activity of cdks by binding to them.

Several cdks and cyclins have been identified in mammals. At present, 9 cdks are known, and they are referred to as "cdk1", "cdk2", and so on. Ten families cyclins are currently recognized, and are referred to as "cyclin A", "cyclin B", and so forth through "cyclin J". For a general review of cyclins see Coats et al. (in *Signal Transduction*, Heldin and Purton, eds., Chapman and Hall, publishers {1996}; pages 347–360) and Lees (*Curr. Opinions Cell Biol.*, 7:773–780 [1995]).

Each cyclin family may have more than one member. Mammals, for example, have two types of cyclin A; cyclin A1 and cyclin A2, and three types of cyclin D (D1, D2, and D3). Prior to the present invention, only one mammalian cyclin E, cyclin E1, was known, although Zariwala et al. (*Pathways to Cancer*, a Cold Spring Harbor Winter Conference, Harlow et al., eds., Cold Spring Harbor Laboratory Press, Cold Spring Harbor, N.Y. p. 49 [1998]) have purportedly identified a novel cyclin E protein. No DNA or amino acid sequence data regarding this molecule is available.

Cyclin family members are typically classified based on their amino acid sequence homology to existing family members. For example, cyclin A2 has about 45 percent amino acid sequence homology to cyclin A1, but only about 19 percent sequence homology to cyclin D1 and 21 percent sequence homology to cyclin E1 (as calculated using the MacVector® clustal alignment software program from Oxford Molecular Group).

All cyclin molecules contain an amino acid sequence domain referred to as the "cyclin box". The cyclin box is about 100 amino acids in length (the average full length of a cyclin polypeptide is 300–500 amino acids) and is located in the middle portion of each cyclin. While the precise amino acid sequence of the cyclin box varies from family to family, and even within members of a family, there is a highly conserved motif within the cyclin box that is consistently present in all cyclin boxes (see Prosite public database, accession number PS00292 which sets forth a cyclin box "consensus" sequence).

Cyclins and cdks bind to each other in a highly selective manner; not all cyclins bind to all cdks. For example, cyclin D1 can associate with cdk4, but not with cdk2. Similarly, cyclin E can associate with cdk2 and cdk3, but not with cdk4; cyclin A can associate with cdk2, but not with cdk5. Formation of cyclin-cdk complexes is transient; the two molecules may be present in the cell at the same time, but can only form an active complex if cdk is phosphorylated by an enzyme referred to as "cak" for cdk activating kinase.

B. Cyclin E1

Human cyclin E1 was first cloned in 1991 and was found to bind to and activate cdk2 (U.S. Pat. No. 5,449,755 issued Sep. 12, 1995; WO 93/06123 published Apr. 1, 1993; Koff et al., *Cell*, 66:1217–1228 [1991]; see also PCT patent application WO 98/03649, published Jan. 29, 1998). Cyclin E1 homologs have been identified in Drosophila (Richardson et al., *Development*, 119:673–690 [1993]), mouse (Damjanov et al., *Biochem. Biophys. Res. Comm.*, 201:994–1000 [1994], Xenopus (Chevalier et al., *J. Cell Sci.*, 109:1173–1184 [1996]) and Zebrafish (Yarden et al., *Devel. Dynam.* 206:1–11 [1996]).In addition, two cyclin E1 variants have been reported. The first of these is a human cyclin E1 splice variant (Mumberg et al., *Nuc. Acids Res.*, 25:2098–2105 1997]) that purportedly has an internal deletion of 45 amino acids, and has an expression pattern that is distinct from full length cyclin E1. The other reported variant purportedly lacks the 15 amino acids at the amino terminus (Ohtsubo et al., *Mol. Cell. Biol.*, 15:2612–2624 [1995]).

A novel cyclin polypeptide, called cyclin N, that purportedly is related to cyclin E1 has recently been reported (Lauper et al., *Abstracts from the* 1998 *Cold Spring Harbor Laboratory Cell Cycle Meeting*, Cold Spring Harbor Laboratory Press, Cold Spring Harbor, N.Y. [1998] p. 115).

C. Cyclins and Cancer

One hallmark of cancer is the uncontrolled, and seemingly unregulated, division of cells. The role of cyclins and cdks in regulation of cell division suggests that these proteins may be involved in converting normal cells to cancerous cells. Numerous recent studies have thus focused on cyclin and cdk involvement in cancer. For example, in a recent review article, Sherr (*Science*, 274:1672–1677 [1996]) pointed out that overexpression of cyclin D1 is seen in sarcomas, colorectal tumors, and melanomas, and that cyclin E is overexpressed in breast, stomach, colon and endometrial carcinomas.

Sarcevic et al. (*J. Biol. Chem.*, 272:33327–33337 [1997]) describe the substrate specificies of various cyclin-cdk complexes in T-47D human breast cancer cells. They found, for example, that cyclin D1-cdk4 phosphorylated a 38 kDa protein, while cyclin D3-cdk4 phosphorylated a 105 kDa protein, a 102 kDa protein, and a 42 kDa protein. Cyclin E1-cdk2 and cyclin A-cdk2 phosphorylated several proteins.

Cyclin E1 has been implicated in breast cancer. In young breast cancer patients, high cyclin E1 expression in breast tumor tissue purportedly correlates with decreased survival (Porter et al., *Nature Med.*, 3:222–225 [1997]). In addition, cyclin E1 is apparently overexpressed in various breast cancer cell lines (Gray-Bablin et al., *Proc. Natl. Acad. Sci USA*, 93:15215–15220 [1996]).

Given that cyclin-cdk complexes are involved in cell division and are active in cancer cells, inactivation of these complexes could result in decreased tumor cell proliferation. U.S. Pat. No. 5,645,999 issued Jul. 8, 1997 describes assays that are purportedly useful for identifying compounds that modulate cyclin E1 activity.

A few naturally occurring proteins have been identified as inhibitors of cyclin-cdk activity. These include the proteins p21 and p27 (U.S. Pat. No. 5,688,665 issued Nov. 18, 1997; PCT WO96/02140, published Feb. 1, 1996; Sherr et al., Genes and Devel., 9:1149–1163 [1995]). The protein p21 purportedly binds directly to cdk1, cdk2, and cdk4, and can apparently inhibit both cyclin D-cdk complexes and cyclin E-cdk complexes (Sherr et al., supra). The protein p27 purportedly binds to cyclin-cdk complexes (rather than to isolated cdks) and can apparently inhibit cyclin A, B, D and E dependent kinase activity (Sherr et al., supra). However, cyclin E1-cdk2 has also been found to purportedly regulate p27 (Sheaff et al., Genes and Devel., 11:1464–1478 [1997]).

In view of the devastating effects of cancer, there is a need in the art to identify molecules in the human body which may have an important role in the etiology of this disease, and to manipulate the expression of such molecules in patients suffering from these and related diseases.

Accordingly, it is an object of this invention to provide nucleic acid molecules and polypeptides that have a role in cell division.

It is a further object to provide methods of altering the level of expression and/or activity of such polypeptides in the human body. related objects will readily be apparent from a reading of this disclosure.

SUMMARY OF THE INVENTION

In one embodiment, the present invention provides an isolated biologically active cyclin E2 nucleic acid molecule encoding a polypeptide selected from the group consisting of the nucleic acid molecule comprising SEQ ID NO:1; the nucleic acid molecule comprising SEQ ID NO:2; the nucleic acid molecule comprising SEQ ID NO:5; the nucleic acid molecule comprising SEQ ID NO:7; the nucleic acid molecule comprising SEQ ID NO:8; a nucleic acid molecule encoding the polypeptide of SEQ ID NO:3, or a biologically active fragment thereof; a nucleic acid molecule encoding the polypeptide of SEQ ID NO:4, or a biologically active fragment thereof; a nucleic acid molecule encoding the polypeptide of SEQ ID NO:6, or a biologically active fragment thereof; a nucleic acid molecule that encodes a polypeptide that is at least 70 percent identical to the polypeptide of SEQ ID NO:1; a nucleic acid molecule that encodes a polypeptide that is at least 70 percent identical to the polypeptide of SEQ ID NO:5; a nucleic acid molecule that hybridizes under conditions of high stringency to any of the nucleic acids above; and an isolated nucleic acid molecule that is the complement of the nucleic acid molecules above.

In another embodiment, the present invention provides vectors comprising the nucleic acids, and host cells comprising the vectors.

In yet another embodiment, the invention provides a process for producing a cyclin E1 polypeptide comprising the steps of expressing a polypeptide encoded by cyclin E2 nucleic acid molecule in a suitable host cell and isolating the polypeptide.

In yet another embodiment, the invention provides a cyclin E2 polypeptide selected from the group consisting of: the polypeptide of SEQ ID NO:3, the polypeptide of SEQ ID NO:4, the polypeptide of SEQ ID NO:6, and a polypeptide that is at least 70 percent identical to any of SEQ ID NO:3, 4, or 5, wherein the cyclin E2 polypeptide may or may not have an amino terminal methionine.

In one other embodiment, the present invention provides a method of increasing proliferation of a cell, comprising expressing a nucleic acid encoding cyclin E2 or a biologically active fragment thereof, in the cell.

In still a further embodiment, the present invention provides a method of increasing cell division of a cell, comprising expressing a cyclin E2 gene, or a biologically active fragment thereof, in the cell.

The invention further proves a method of decreasing cell division in a cell, comprising expressing a cyclin E2 mutant in a cell, wherein the mutant does not have cyclin E2 biological activity.

BRIEF DESCRIPTION OF THE DRAWINGS

FIGS. 1 depicts the full length cDNA sequence of human cyclin E2 (SEQ ID NO:1).

FIGS. 2 depicts the full length cDNA sequence of mouse cyclin E2 (SEQ ID NO:2).

FIGS. 3 depicts the putative full length amino acid sequence (SEQ ID NO:3) of human cyclin E2 as translated from the cDNA sequence.

FIGS. 4 depicts the putative full length amino acid sequence (SEQ ID NO:4) of mouse cyclin E2 as translated from the cDNA sequence.

FIG. 5 depicts the full length cDNA sequence of a human cyclin E2 splice variant (SEQ ID NO:5).

FIG. 6 depicts the putative full length amino acid sequence (SEQ ID NO:6) of the human cyclin E2 splice variant encoded by the DNA of SEQ ID NO:5.

FIG. 7 depicts the sequence of a DNA molecule (SEQ ID NO:7) encoding full length human cyclin E2 in which the codons have been optimized for expression in E. coli cells.

FIG. 8 depicts the sequence of a DNA molecule (SEQ ID NO:18) encoding full length mouse cyclin E2 in which the codons have been optimized for expression in E. coli cells.

FIGS. 10A–10E are photographs of Western blots (10A–D) and an autorad (10E). Human cells were transfected with various DNA constructs as indicated at the bottom of the panels. "pEGFP" refers to the GFP vector; "HA-cdk2" refers to hemagluttinin-tagged cdk2; "p27" refers to a vector containing human p27 cDNA; "GFP-E2" refers to a vector containing GFP DNA fused to full length cyclin E2 cDNA; and "GFP-E2sv" refers to a vector containing GFP DNA fused to human cyclin E2 splice variant cDNA. For all panels, the transfected cells were lysed. In 10A–D, the cell lysates were treated with anti-GFP antiserum after which Protein A-Sepharose beads were added to immunoprecipitate the anti-GFP antibody. Immunoprecipitate was run on a gel, transferred to a Western blot, and probed with the antibody indicated to the left of each panel. For 10E, histone H1 and 32P-ATP were added to the cell extract, incubated for about 30 minutes at room temperature, and the mixture was then run on SDS-PAGE. The gel was then exposed to film for 2 hours. The identity of each band on the Western blots and autorad is indicated on the right of each panel.

FIG. 11 depicts an "ambiguous sequence" of human cyclin E2 (SEQ ID NO:8); this sequence identifies those codons that can be changed for optimal expression of the DNA in both eukaryotic and prokaryotic host cells. In this Figure, the letters B, D, H, K, M, R, S, V, W, Y, and N have the standard IUPAC meaning for nucleotides.

FIG. 12 is a bar graph of a Northern blot which quantitates mRNA expression levels of human cyclin E2, human cyclin E1, and the enzyme GADPH (as a control) in various human tissues. The human tissues are indicated on the x-axis. The bar graph was generated by computer scan of the Northern blot after probing with each probe. Cyclin E1, cyclin E2, and GADPH are indicated.

FIG. 13 is a Northern blot of human breast tumor derived cell lines probed with cyclin E1 and cyclin E2 probes. "Normal" refers to normal immortalized cells. Estrogen receptor positive ("ER+") and estrogen receptor negative ("ER−") tumor derived cell lines are indicated. The name of each cell line is indicated at the top of the blot.

FIG. 14 depicts an "ambiguous sequence" of mouse cyclin E2 (SEQ ID NO:19); this sequence identifies those codons that can be changed for optimal expression of the DNA in both eukaryotic and prokaryotic host cells. The letters have the standard IUPAC meaning for nucleotides.

DETAILED DESCRIPTION OF THE INVENTION

Figure 9:
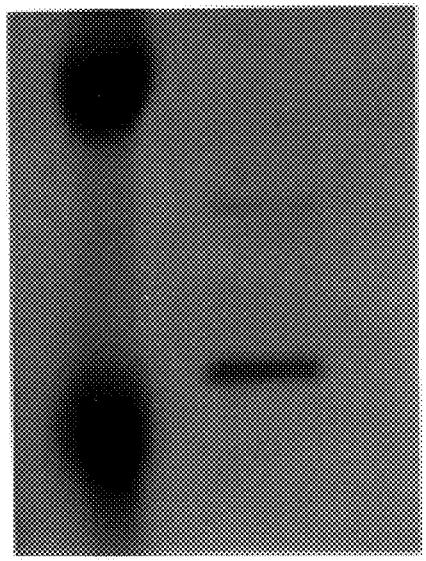
FIG. 9 is a photograph of a Coomassie stained SDS gel. "Stds" refers to prestained molecular weight standards of the indicated molecular weights, and "Cyc E2" refers to human cyclin E2 polypeptide.

Included in the scope of this invention are cyclin E2 polypeptides such as the polypeptides of SEQ ID NO:3 and SEQ ID NO:4, and related biologically active polypeptide fragments, variants, and derivatives thereof. These cyclin E2 polypeptides share a homology of only about 47 percent with cyclin E1 polypeptides at the amino acid level and about 55 percent at the DNA level.

Included within the scope of the present invention are nucleic acid molecules that encode cyclin E2 polypeptides, and methods for preparing the polypeptides.

Also included within the scope of the present invention are non-human mammals such as mice, rats, rabbits, goats, or sheep in which the gene (or genes) encoding native cyclin E2 has (have) been disrupted ("knocked out") such that the level of expression of this gene or genes is (are) significantly decreased or completely abolished. Such mammals may be prepared using techniques and methods such as those described in U.S. Pat. No. 5,557,032. The present invention further includes non-human mammals such as mice, rats, rabbits, goats, or sheep in which the gene (or genes) encoding cyclin E2 (either the native form of cyclin E2 for the mammal or a heterologous cyclin E2 gene(s)) is (are) over expressed by the mammal, thereby creating a "transgenic" mammal. Such transgenic mammals may be prepared using well known methods such as those described in U.S. Pat. No 5,489,743 and PCT patent application no. WO94/28122, published Dec. 8, 1994. The present invention further includes non-human mammals in which the cyclin E2 promoter is either activated or inactivated (using homologous recombination methods as described below) to alter the level of expression of native cyclin E2.

The cyclin E2 polypeptides of the present invention may be added to cells to enhance cell division. Alternatively, cyclin E2 polypeptide activity in a cell may be inhibited or inactivated in to decrease or stop cell division of certain cells.

The term "cyclin E2 protein" or "cyclin E2 polypeptide" as used herein refers to any protein or polypeptide having the properties described herein for cyclin E2. The small letter in front of the term "cyclin E2", when used, refers to a cyclin E2 polypeptide from a particular mammal, i.e., "h-cyclin E2" refers to human cyclin E2, and "m-cyclin E2" refers to mouse cyclin E2. The cyclin E2 polypeptide may or may not have an amino terminal methionine, depending on the manner in which it is prepared. By way of illustration, cyclin E2 protein or cyclin E2 polypeptide refers to (1) a biologically active polypeptide encoded by cyclin E2 nucleic acid molecules as defined in any of items (a)–(f) below, and biologically active peptide or polypeptide fragments thereof; (2) naturally occurring allelic variants and synthetic variants of the cyclin E2 gene which encode a cyclin E2 polypeptide that has one or more amino acid substitutions deletions, and/or insertions as compared to the cyclin E2 polypeptide of SEQ ID NO:3 or SEQ ID NO:4, and/or (3) biologically active polypeptides, or fragments or variants thereof, that have been chemically modified.

As used herein, the term "cyclin E2 fragment" refers to a peptide or polypeptide that is less than the full length amino acid sequence of naturally occurring cyclin E2 protein but has cyclin E2 biological activity. Such a fragment may be truncated at the amino terminus, the carboxy terminus, and/or internally (such as by natural splicing), and may be a variant or a derivative of cyclin E2. Such cyclin E2 fragments may be prepared with or without an amino terminal methionine. In addition, cyclin E2 fragments can be naturally occurring fragments such as the cyclin E2 splice variant (SEQ ID NO:5), other splice variants, and fragments resulting from in vivo protease activity.

As used herein, the term "cyclin E2 variant" refers to a cyclin E2 polypeptide whose amino acid sequence contains one or more amino acid sequence substitutions, deletions, and/or insertions as compared to the cyclin E2 amino acid sequence set forth in SEQ ID NOS: 3 and 4. Such cyclin E2 variants can be prepared from the corresponding cyclin E2 nucleic acid molecule variants, which have a DNA sequence that varies accordingly from the DNA sequences for wild type cyclin E2 as set forth in SEQ ID NOS: 1 and 2. Preferred variants of the human cyclin E2 polypeptide include alanine substitutions at one or more of amino acid positions 12–23, 32–53, 350–357, and 395–404 which can serve to alter the substrate specificity of the cyclin E2 polypeptide. Other preferred variants include alanine substitutions at amino acids positions 392, 396, 397, and/or 401, which mutants can serve to increase the stability of the polypeptide.

As used herein, the term "cyclin E2 derivative" refers to a cyclin E2 polypeptide, protein, or fragment that has been chemically modified, as for example, by addition of one or more polyethylene glycol molecules, sugars, phosphates, and/or other such molecules, where the molecule or molecules are not naturally attached to wild-type cyclin E2 polypeptide.

As used herein, the terms "biologically active cyclin E2 polypeptide", "biologically active cyclin E2 fragment", "biologically active cyclin E2 variant", and "biologically active cyclin E2 derivative" refer to a cyclin E2 polypeptide that naturally forms a complex with cyclin dependent kinase 2 ("cdk2") and is capable of phosphorylating the retinoblastoma ("Rb") gene product.

As used herein, the term "cyclin E2 " when used to describe a nucleic acid molecule refers to a nucleic acid molecule or fragment thereof that (a) has the nucleotide sequence as set forth in SEQ ID NO:1 or SEQ ID NO:2; (b) has a nucleic acid sequence encoding a polypeptide that is at least 70 percent identical, but may be greater than 70 percent, i.e., 75, 80, 85, 90, 95 percent, or even greater than 95 percent identical, to the polypeptide encoded by any of SEQ ID NOS:1 or 2; (c) is a naturally occurring allelic variant of (a) or (b); (d) is a nucleic acid variant of (a)–(c) produced as provided for herein;(e) has a sequence that is complementary to (a)–(d); and/or (f) hybridizes to any of (a)–(e) under conditions of high stringency.

Percent sequence identity can be determined by standard methods that are commonly used to compare the similarity in position of the amino acids of two polypeptides. By way of example, using a computer algorithm such as BLAST, BLAST2, or FASTA, the two polypeptides for which the percent sequence identity is to be determined are aligned for optimal matching of their respective amino acids (the "matched span", which can include the full length of one or both sequences, or a pre-determined portion of one or both sequences). Each computer program provides a "default" opening penalty and a "default" gap penalty, and a scoring matrix such as PAM 250 (for FASTA) or BLOSUM 62 (for BLAST algorithms). A preferred algorithm is BLAST2.

A standard scoring matrix (see Dayhoff et al., in: *Atlas of Protein Sequence and Structure,* vol. 5, supp.3 [1978]) can be used in conjunction with the computer algorithm. The percent identity can then be calculated by determining the percent identity using an algorithm contained in a program such as FASTA:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 70 percent identical will typically have one or more amino acid substitutions, deletions, and/or insertions as compared with wild type cyclin E2. Usually, the substitutions of the native residue will be either alanine, or a conservative amino acid so as to have little or no effect on the overall net charge, polarity, or hydrophobicity of the protein. Conservative substitutions are set forth in Table I below.

TABLE I

Conservative Amino Acid Substitutions

| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

The term "conditions of high stringency" refers to hybridization and washing under conditions that permit binding of a nucleic acid molecule used for screening, such as an oligonucleotide probe or cDNA molecule probe, to highly homologous sequences. An exemplary high stringency wash solution is 0.2× SSC and 0.1 percent SDS used at a temperature of between 50° C.–65° C.

Where oligonucleotide probes are used to screen cDNA or genomic libraries, one of the following two high stringency solution may be used. The first of these is 6× SSC with 0.05 percent sodium pyrophosphate at a temperature of 35° C.–62° C., depending on the length of the oligonucleotide probe. For example, 14 base pair probes are washed at 35–40° C., 17 base pair probes are washed at 45–50° C., 20 base pair probes are washed at 52–57° C., and 23 base pair probes are washed at 57–63° C. The temperature can be increased 2–3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45–50° C.

As used herein, the terms "effective amount" and "therapeutically effective amount" refer to the amount of cyclin E2 necessary to support one or more biological activities of cyclin E2 as set forth above.

A full length cyclin E2 polypeptide or fragment thereof can be prepared using well known recombinant DNA technology methods such as those set forth in Sambrook et al. (*Molecular Cloning: A Laboratory Manual,* Cold Spring Harbor Laboratory Press, Cold Spring Harbor, N.Y. [1989]) and/or Ausubel et al., eds, (*Current Protocols in Molecular Biology,* Green Publishers Inc. and Wiley and Sons, New York [1994]). A gene or cDNA encoding a cyclin E2 protein or fragment thereof may be obtained for example by screening a genomic or cDNA library, or by PCR amplification. Probes or primers useful for screening the library can be generated based on sequence information for other known genes or gene fragments from the same or a related family of genes, such as, for example, conserved motifs found in other cyclin genes such as the cyclin box. In addition, where a cyclin gene has been identified from one species, all or a portion of that gene may be used as a probe to identify homologous genes from other species. The probes or primers may be used to screen CDNA libraries from various tissue sources believed to express the cyclin E2 gene. Typically, conditions of high stringency will be employed for screening to minimize the number of false positives obtained from the screen.

Another means to prepare a gene encoding cyclin E2 polypeptide or fragment thereof is to employ chemical synthesis using methods well known to the skilled artisan such as those described by Engels et al.(*Angew. Chem. Intl. Ed.,* 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the cyclin E2 polypeptide will be several hundred nucleotides in length. Nucleic acids larger than about 100 nucleotides can be synthesized as several fragments using these methods. The fragments can then be ligated together to form the full length cyclin E2 polypeptide. Usually, the DNA fragment encoding the amino terminus of the polypeptide will have an ATG, which encodes a methionine residue. This methionine may or may not be present on the mature form of the cyclin E2 polypeptide, depending on whether the polypeptide produced in the host cell is secreted from that cell.

In some cases, it may be desirable to prepare nucleic acid and/or amino acid variants of naturally occurring cyclin E2. Nucleic acid variants (wherein one or more nucleotides are designed to differ from the wild-type or naturally occurring cyclin E2) may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce cyclin E2. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s) on cyclin E2, or those designed to delete an existing glycosylation and/or phosphorylation site(s) on cyclin E2.

The cyclin E2 gene, cDNA, or fragment thereof can be inserted into an appropriate expression or amplification vector using standard ligation techniques. The vector is typically selected to be functional in the particular host cell employed (i.e., the vector is compatible with the host cell machinery such that amplification of the cyclin E2 gene and/or expression of the gene can occur). The cyclin E2 gene, CDNA or fragment thereof may be amplified/expressed in prokaryotic, yeast, insect (baculovirus systems) and/or eukaryotic host cells. Selection of the host cell will depend in part on whether the cyclin E2 polypeptide or fragment thereof is to be glycosylated and/or phosphorylated. If so, yeast, insect, or mammalian host cells are preferable.

Typically, the vectors used in any of the host cells will contain 5' flanking sequence (also referred to as a "promoter") and other regulatory as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide molecule located at the 5' or 3' end of the cyclin E2 coding sequence; the oligonucleotide molecule encodes polyHis (such as hexaHis), or other "tag" such as FLAG, HA (hemaglutinin Influenza virus) or myc for which commercially available antibodies exist. This tag is typically fused to the protein, and can serve as an tag for affinity purification of the cyclin E2 polypeptide from the host cell. Affinity purification can be accomplished, for example, by column chromatography using antibodies against the tag as an affinity matrix. Optionally, the tag can subsequently be removed from the purified cyclin E2 polypeptide by various means such as using certain peptidases.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native cyclin E2 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the cyclin E2 flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the cyclin E2 polypeptide. If the vector of choice does not contain an origin of replication site, one may be chemically synthesized based on a known sequence, and ligated into the vector.

The transcription termination element is typically located 3' of the end of the cyclin E2 polypeptide coding sequence and serves to terminate transcription of the cyclin E2 polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the cyclin E2 polypeptide to be synthesized. The Shine-Dalgarno sequence is varied but is typically a polypurine (i.e., having a high A–G content). Many Shine-Dalgarno sequences have been identified, each of which can be readily synthesized using methods set forth above and used in a prokaryotic vector.

In those cases where it is desirable for cyclin E2 polypeptide to be secreted from the host cell, a signal sequence may be used to direct the cyclin E2 polypeptide out of the host cell where it is synthesized, and the carboxy-terminal part of the protein may be deleted in order to prevent membrane anchoring. Typically, the signal sequence is positioned in the coding region of the cyclin E2 nucleic acid sequence, or directly at the 5' end of the cyclin E2 coding region. Many signal sequences have been identified, and any of them that are functional in the selected host cell may be used in conjunction with the cyclin E2 gene. Therefore, the signal sequence may be homologous or heterologous to the cyclin E2 gene, and may be homologous or heterologous to the cyclin E2 gene. Additionally, the signal sequence may be chemically synthesized using methods set forth above.

In most cases, secretion of the polypeptide from the host cell via the presence of a signal peptide will result in the removal of the amino terminal methionine from the polypeptide.

In many cases, transcription of the cyclin E2 gene is increased by the presence of one or more introns in the vector; this is particularly true where cyclin E2 is produced in eukaryotic host cells, especially mammalian host cells. The introns used may be naturally occurring within the cyclin E2 gene, especially where the cyclin E2 gene used is a full length genomic sequence or a fragment thereof. Where the intron is not naturally occurring within the cyclin E2 gene (as for most cDNAs), the intron(s) may be obtained from another source. The position of the intron with respect to the 5' flanking sequence and the cyclin E2 gene is generally important, as the intron must be transcribed to be effective. As such, where the cyclin E2 gene inserted into the expression vector is a cDNA molecule, the preferred position for the intron is 3' to the transcription start site, and 5' to the polyA transcription termination sequence. Preferably for cyclin E2 cDNA, the intron will be located on one side or the other (i.e., 5' or 3') of the cDNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII, pCR3, and pcDNA3 (Invitrogen Company, San Diego, Calif.), pBSII (Stratagene Company, LaJolla, Calif.), pET15b (Novagen, Madison, Wis.), pGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

After the vector has been constructed and a nucleic acid molecule encoding full length or truncated cyclin E2 has been inserted into the proper site of the vector, the completed vector may be inserted into a suitable host cell for amplification and/or cyclin E2 polypeptide expression.

Host cells may be prokaryotic host cells (such as *E. coli*) or eukaryotic host cells (such as a yeast cell, an insect cell, or a vertebrate cell). The host cell, when cultured under appropriate conditions, synthesize cyclin E2 polypeptide which can subsequently be collected from the culture medium (if the host cell secretes it into the medium) or directly from the host cell producing it (if it is not secreted). After collection, the cyclin E2 polypeptide can be purified using methods such as molecular sieve chromatography, affinity chromatography, and the like.

Selection of the host cell for cyclin E2 polypeptide production will depend in part on whether the cyclin E2 polypeptide is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize cyclin E2 polypeptide that has biological activity, the cyclin E2 polypeptide may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of E. coli (e.g., HB101, DH5α,DH10, and MC1061) are well-known as host cells in the field of biotechnology. Various strains of B. subtilis, Pseudomonas spp., other Bacillus spp., Streptomyces spp., and the like may also be employed in this method.

Many strains of yeast cells known to those skilled in the art are also available as host cells for expression of the polypeptides of the present invention.

Additionally, where desired, insect cell systems may be utilized in the methods of the present invention. Such systems are described for example in Kitts et al. (Biotechniques, 14:810–817 [1993]), Lucklow (Curr. Opin. Biotechnol., 4:564–572 [1993])and Lucklow et al. (J. Virol., 67:4566–4579 [1993]). Preferred insect cells are Sf-9 and Hi5 (Invitrogen, Carlsbad, Calif.).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing E. coli cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of cyclin E2 polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the cyclin E2 polypeptide has been designed to be secreted from the host cells, the majority of polypeptide may be found in the cell culture medium. Polypeptides prepared in this way will typically not possess an amino terminal methionine, as it is removed during secretion from the cell. If however, the cyclin E2 polypeptide is not secreted from the host cells, it will be present in the cytoplasm and/or the nucleus (for eukaryotic host cells) or in the periplasm (for gram negative bacteria host cells) and may have an amino terminal methionine.

For cyclin E2 polypeptide situated in the host cell cytoplasm and/or nucleus, the host cells are typically first disrupted mechanically or with detergent to release the intra-cellular contents into a buffered solution. Cyclin E2 polypeptide can then be isolated from this solution.

Purification of cyclin E2 polypeptide from solution can be accomplished using a variety of techniques. If the polypeptide has been synthesized such that it contains a tag such as Hexahistidine (cyclin E2/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing cyclin E2). For example, polyhistidine binds with great affinity and specificity to nickel, thus an affinity column of nickel (such as the Qiagen® nickel columns) can be used for purification of cyclin E2/polyHis. (See for example, Ausubel et al., eds., Current Protocols in Molecular Biology, Section 10.11.8, John Wiley & Sons, New York [1993]).

Where the cyclin E2 polypeptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the cyclin E2 polypeptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If the cyclin E2 polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The cyclin E2 polypeptide in its now soluble form can then be analyzed using gel electrophoresis, immunoprecipitation or the like. If it is desired to isolate the cyclin E2 polypeptide, isolation may be accomplished using standard methods such as those set forth below and in Marston et al. (Meth. Enz., 182:264–275 [1990]).

If cyclin E2 polypeptide inclusion bodies are not formed to a significant degree in the periplasm of the host cell, the cyclin E2 polypeptide will be found primarily in the supernatant after centrifugation of the cell homogenate, and the cyclin E2 polypeptide can be isolated from the supernatant using methods such as those set forth below.

In those situations where it is preferable to partially or completely isolate the cyclin E2 polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying cyclin E2 polypeptide using recombinant DNA techniques, the cyclin E2 polypeptides, fragments, and/or derivatives thereof may be prepared by chemical synthesis methods (such as solid phase peptide synthesis) using techniques known in the art such as those set forth by Merrifield et al., (*J. Am. Chem. Soc.,* 85:2149 [1963]), Houghten et al. (*Proc Natl Acad. Sci. USA,* 82:5132 [1985]), and Stewart and Young (Solid Phase Peptide Synthesis, Pierce Chemical Co., Rockford, Ill. [1984]). Such polypeptides may be synthesized with or without a methionine on the amino terminus. Chemically synthesized cyclin E2 polypeptides or fragments may be oxidized using methods set forth in these references to form disulfide bridges. The cyclin E2 polypeptides or fragments are expected to have biological activity comparable to cyclin E2 polypeptides produced recombinantly or purified from natural sources, and thus may be used interchangably with recombinant or natural cyclin E2 polypeptide.

Chemically modified cyclin E2 compositions in which cyclin E2 polypeptide is linked to a polymer are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of cyclin E2 polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1–C10 alkoxy or aryloxy derivatives thereof (see U.S. Pat. No. 5,252,714).

Pegylation of cyclin E2 may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable conditions used to react a biologically active substance with an activated polymer molecule. Methods for preparing pegylated cyclin E2 will generally comprise the steps of (a) reacting a cyclin E2 polypeptide with polyethylene glycol (such as a reactive ester or aldehyde derivative of PEG) under conditions whereby cyclin E2 becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Generally, conditions which may be alleviated or modulated by administration of the present polymer/cyclin E2 polypeptides include those described herein for cyclin E2 molecules. However, the polymer/cyclin E2 molecules disclosed herein may have additional activities, enhanced or reduced biological activity, or other characteristics, such as increased or decreased half-life, as compared to the non-derivatized molecules.

The cyclin E2 polypeptides, fragments thereof, variants, and derivatives, may be employed alone, together, or in combination with other pharmaceutical compositions. The cyclin E2 polypeptides, fragments, variants, and derivatives may be used in combination with cytokines, growth factors, antibiotics, anti-inflammatories, and/or chemotherapeutic agents as is appropriate for the indication being treated.

The cyclin E2 molecules, whether administered alone or in combination therapy, may be useful in promoting cell division of particular cell populations such as white blood cells, red blood cells, neurons, chondrocytes, and the like. In AIDS patients and cancer patients that have undergone chemotherapy and/or bone marrow transplants, the white blood cell count is typically low; administration of cyclin E2 to the patient's stem cells and/or other white blood cells, either by gene therapy or by direct treatment of the cells with cyclin E2 in an ex vivo manner, could serve to increase the white blood cell count. Similarly, in hemophiliacs and kidney dialysis patients, for example, treatment of the patient's progenitor erythroblast cell population with cyclin E2 via gene therapy or ex vivo treatment, could enhance red blood cell count. Another indication in which cyclin E2 administration could be useful is to increase chondrocytes in patients suffering from degeneration of cartilage due to joint injury, arthritis, or the like. Here, cyclin E2 could be administered to chondrocytes either via gene therapy or by ex vivo treatment of cultured chondrocytes. Still another indication for cyclin E2 therapy would be to expand the population of neurons in patients suffering from Alzheimer's disease, or other neurological disorders that result from apoptosis of various neurons. Finally, cyclin E2 therapy could be indicated in stroke or ischemia in which tissue damage results from loss of blood flow. Here, administration of cyclin E2 to cells surrounding the area of necrosis could serve to regenerate the necrotic tissue.

Cyclin E2 nucleic acid molecules, fragments, and/or derivatives that do not themselves encode polypeptides that are active in activity assays may be useful as hybridization probes in diagnostic assays to test, either qualitatively or quantitatively, for the presence of cyclin E2 DNA or corresponding RNA in mammalian tissue or bodily fluid samples.

Cyclin E2 polypeptide fragments, variants, and/or derivatives that are not themselves active in activity assays may be useful for preparing antibodies that recognize cyclin E2 polypeptides.

The cyclin E2 polypeptides, fragments, variants, and/or derivatives may be used to prepare antibodies using standard methods. Thus, antibodies that react with the cyclin E2 polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will either be of human origin, or will be "humanized", i.e., prepared so as to prevent or minimize an immune reaction to the antibody when administered to a patient. The antibody fragment may be any fragment that is reactive with the cyclin E2 polypeptides of the present invention, such as, $F_{ab}$, $F_{ab'}$, etc. Also provided by this invention are the hybridomas generated by presenting cyclin E2 or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human cyclin E2 polypeptide of the present invention are also encompassed by this invention.

The antibodies may be used therapeutically, such as to inhibit binding of cyclin E2 to cdk2. The antibodies may further be used for in vivo and in vitro diagnostic purposes, such as in labeled form to detect the presence of cyclin E2 in a body fluid or cell sample.

Preferred antibodies are human antibodies, either polyclonal or monoclonal.

Therapeutic Compositions and Administration

Therapeutic compositions of cyclin E2 are within the scope of the present invention. Such compositions may comprise a therapeutically effective amount of cyclin polypeptide, fragments, variants, or derivatives in admixture with a pharmaceutically acceptable carrier. The carrier material may be water for injection, preferably supplemented with other materials common in solutions for administration to mammals. Typically, a cyclin E2 therapeutic compound will be administered in the form of a composition comprising purified cyclin E2 polypeptide, fragment, variant, or derivative in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

The cyclin E2 compositions can be administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of cyclin E2 compositions useful for practicing the present invention may be prepared for storage by mixing the selected composition having the desired degree of purity with optional physiologically acceptable carriers, excipients, or stabilizers (*Remington's Pharmaceutical Sciences*, 18th Edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the cyclin E2 composition(s) to be employed therapeutically will depend, for example, upon the therapeutic objectives such as the indication for which cyclin E2 is being used, the route of administration, and the condition of the patient. Accordingly, it will be necessary for the therapist to titer the dosage and modify the route of administration as required to obtain the optimal therapeutic effect. A typical daily dosage may range from about 0.1 μg/kg to up to 100 mg/kg or more, depending on the factors mentioned above. Typically, a clinician will administer the cyclin E2 composition until a dosage is reached that achieves the desired effect. The cyclin E2 composition may therefore be administered as a single dose, or as two or more doses (which may or may not contain the same amount of cyclin E2) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The cyclin E2 composition to be used for in vivo administration must be sterile. This is readily accomplished by filtration through sterile filtration membranes. Where the cyclin E2 composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

Alternatively or additionally, cyclin E2 may be administered locally via implantation into the affected area of a membrane, sponge, or other appropriate material on to which cyclin E2 polypeptide has been absorbed.

Where an implantation device is used, the device may be implanted into any suitable tissue or organ, and delivery of cyclin E2 may be directly through the device via bolus, or via continuous administration, or via catheter using continuous infusion.

Cyclin E2 polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547–556 [1983]), poly (2-hydroxyethyl-methacrylate) (Langer et al., *J. Biomed. Mater. Res.,* 15: 167–277 [1981] and Langer, *Chem. Tech.,* 12: 98–105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., Epstein et al., *Proc. Natl. Acad. Sci. USA,* 82: 3688–3692 [1985]; EP 36,676; EP 88,046; EP 143,949).

In some cases, it may be desirable to use cyclin E2 compositions in an ex vivo manner. Here, cells, tissues, or organs that have been removed from the patient are exposed to cyclin E2 compositions after which the cells, tissues and/or organs are subsequently implanted back into the patient.

In other cases, cyclin E2 may be delivered through implanting into patients certain cells that have been genetically engineered, using methods such as those described herein, to express and secrete cyclin E2 polypeptides, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975 (Baetge et al., CytoTherapeutics, Inc.). The cells, with or without encapsulation, may be implanted into suitable body tissues or organs of the patient.

As discussed above, it may be desirable to treat isolated cell populations such as stem cells, lymphocytes, red blood cells, chondrocytes, neurons, and the like with cyclin E2. This can be accomplished by exposing the isolated cells to cyclin E2 protein directly, where the cyclin E2 is in a form that is permeable to the cell membrane. Alternatively, gene therapy can be employed as described below.

One manner in which gene therapy can be applied is to use the cyclin E2 gene (either genomic DNA, cDNA, and/or synthetic DNA encoding cyclin E2, or a fragment, variant, or derivative thereof) which may be operably linked to a constitutive or inducible promoter to form a "gene therapy DNA construct". The promoter may be homologous or heterologous to the endogenous cyclin E2 gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter enhancers or silencers, DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

This gene therapy DNA construct can then be introduced into the patient's cells (either ex vivo or in vivo). One means for introducing the gene therapy DNA construct is via viral vectors. Suitable viral vectors typically used in gene therapy for delivery of gene therapy DNA constructs include, without limitation, adenovirus, adeno-assoicated virus, herpes simplex virus, lentivirus, papilloma virus, and retrovirus vectors. Some of these vectors, such as retroviral vectors, will deliver the gene therapy DNA construct to the chromosomal DNA of the patient's cells, and the gene therapy DNA construct can integrate into the chromosomal DNA; other vectors will function as episomes and the gene therapy DNA construct will remain in the cytoplasm. The use of gene therapy vectors is described, for example, in U.S. Pat. No. 5,672,344 (Sep. 30, 1997; Kelly et al., University of Michigan), U.S. Pat. No. 5,399,346 (Mar. 21, 1995; Anderson et al., U.S Dept. Health and Human Services), U.S. Pat. No. 5,631,236 (May 20, 1997; Woo et al., Baylor College of Medicine), and U.S. Pat. No. 5,635,399 (Jun. 3, 1997; Kriegler et al., Chiron Corp.).

Alternative means to deliver gene therapy DNA constructs to a patient's cells without the use of viral vectors include, without limitation, liposome-mediated transfer, direct injection of naked DNA, receptor-mediated transfer (ligand-DNA complex), electroporation, calcium phosphate precipitation, and microparticle bombardment (e.g., "gene gun"). See U.S. Pat. No. 4,970,154 (Nov. 13, 1990; Chang, Baylor College of Medicine), WO 96/40958 (Dec. 19, 1996; Smith et al., Baylor College of Medicine) U.S. Pat. No. 5,679,559 (Oct. 21, 1997; Kim et al., University of Utah) U.S. Pat. No. 5,676,954 (Oct. 14, 1997; Brigham, Vanderbilt University), and U.S. Pat. No. 5,593,875 (Jan. 14, 1997; Wurm et al., Genentech).

Another means to increase endogenous cyclin E2 expression in a cell via gene therapy is to insert one or more enhancer elements into the cyclin E2 promoters, where the enhancer element(s) can serve to increase transcriptional activity of the cyclin E2 gene. The enhancer element(s) used will be selected based on the tissue in which one desires to activate cyclin E2; enhancer elements known to confer promoter activation in a given tissue will be selected. For example, if cyclin E2 is to be "turned on" in T-cells, the lck promoter enhancer element may be used. Here, the functional portion of the transcriptional element to be added may be inserted into a fragment of DNA containing the cyclin E2 promoter (and optionally, vector, 5' and/or 3' flanking sequence, etc as well) using standard cloning techniques. This construct, known as a "homologous recombination construct" can then be introduced into the desired cells either ex vivo or in vivo.

Gene therapy can be used to decrease cyclin E2 expression by modifying the nucleotide sequence of the endogenous cyclin E2 promoter. Such modification is typically accomplished via homologous recombination methods. For example, a DNA molecule containing all or a portion of the cyclin E2 promoter sequence can be engineered to remove and/or replace pieces of the promoter that regulate transcription. Here, the TATA box and/or the binding site of a transcriptional activator protein of the cyclin E2 promoter may be deleted using standard molecular biology techniques; such deletion can inhibit promoter activity thereby repressing transcription of the corresponding cyclin E2 gene. Deletion of the TATA box or transcription activator binding site in the promoter may be accomplished by generating a DNA construct comprising all or the relevant portion of the cyclin E2 promoter (from the same or a related species as the cyclin E2 gene to be regulated) in which one or more of the TATA box and/or transcriptional activator binding site nucleotides are mutated via substitution, deletion and/or insertion of one or more nucleotides such that the TATA box and/or activator binding site has decreased activity or is rendered completely inactive. This construct, which also will typically contain at least about 500 bases of DNA that corresponds to the native (endogenous) 5' and 3' flanking regions of the promoter segment that has been modified, may be introduced into the appropriate cells (either ex vivo or in vivo) either directly or via a viral vector as described above. Typically, integration of the construct into the genomic DNA of the cells will be via homologous recombination, where the 5' and 3' flanking DNA sequences in the promoter construct can serve to help integrate the modified promoter region via hybridization to the endogenous chromosomal DNA.

Other gene therapy methods may also be employed where it is desirable to inhibit cyclin E2 activity. For example, antisense DNA or RNA molecules, which have a sequence that is complementary to at least a portion of the cyclin E2 can be introduced into the cell. Typically, the antisense molecule will be complementary to the start site (5' end) of the cyclin E2 gene. When the antisense molecule then hybridizes to the cyclin E2 mRNA, translation of the cyclin E2 mRNA is prevented.

Alternatively, gene therapy may be employed to create a dominant-negative inhibitor of cyclin E2. In this situation, the DNA encoding a mutant full length or truncated polypeptide of cyclin E2 can be prepared and introduced into the cells of a patient using either viral or non-viral methods as described above. The cyclin E2 mutant is typically designed to (1) compete with endogenous cyclin E2 in its biological role; and (2) contain one or more insertions, deletions, and/or mutations as compared to wild type cyclin E2 such that it still binds cdk2, but does not permit formation of an active cyclin E2/cdk complex (see, for example Diehl et al., *Mol. Cell. Biol.,* 17:7362–7374 [1997]). This mutant cyclin E2 protein, when overexpressed in the cells into which it is introduced, can compete with endogenous cyclin E2 protein, resulting in the formation of mutant cyclin E2/cdk2 complexes that are inactive.

Biology of Cyclin E2

While not intending to be bound to any one theory, it is believed that, in vivo, cyclin E2 is thought to form a complex with cyclin-dependent kinase 2 ("cdk2") to form a "holoenzyme"; this holoenzyme can then be phosphorylated at position 160 (threonine) of cdk2 by a separate enzyme complex called "cyclin activating kinase" or "cak". Upon phosphorylation of the cdk2 portion of the cyclin E2/cdk holoenzyme complex, this complex can then phosphorylate its substrates, which are retinoblastoma and histone H1 via the kinase activity of the cdk2 portion of the holoenzyme.

Assays to Screen for Inhibitors of Cyclin E2

Organic (biological or synthetic) or inorganic molecules that inhibit cyclin E2 can be identified using one or more of the screening assays described below. Such molecules could be administered either in an ex vivo manner, or in an in vivo manner by local or iv injection, or by oral delivery, implantation device, or the like.

For ease of reading, the following definition is used herein for describing the assays:

"Test molecule(s)" refers to the molecule(s) that is under evaluation as an inhibitor of cyclin E2, either by virtue of its potential ability to block (1) the interaction of cyclin E2 with cyclin dependent kinase ("cdk2"; a molecule with which it naturally associates in the cell; see Examples herein) or (2) the interaction of cyclin E2/cdk2 with cyclin activating kinase "cak"; a molecule that "activates" the cyclin E2/cdk2 complex by phosphorylation of cdk at position 160, but only when cdk2 is complexed with cyclin E2.

A. In Vitro Assays Using Purified Proteins

One type of in vitro assay for evaluating the efficacy of a cyclin E2 inhibitor test molecule requires purified cyclin E2 and cdk. Cyclin E2 polypeptide and cdk polypeptide can be recombinantly produced using methods described above. The gene encoding cdk is known (Ninomiya-Tsuji et al., *Proc. Natl. Acad. Sci. USA,* 88:9006–9010 [1991]; Tsai et al., *Nature,* 353:174–177 [1991]). Recombinant cyclin E2 and cdk2 polypeptides can be full length molecules, or biologically active variants or derivatives thereof. Host cells for recombinant production of each polypeptide include, without limitation, bacteria such as *E. coli,* yeast, insect cells (using, for example, the baculovirus system), mammalian cells, or other eukaryotic cells. The two polypeptides may be co-produced in the same host cell, where the host cell is co-transfected with DNA encoding each polypeptide, or in separate host cells of the same or different species.

Each polypeptide can be purified from the host cell (or culture medium if it is secreted); typically, this will be accomplished by expressing each polypeptide with a "tag" sequence such as hemaglutinin ("HA"), His (polyhistidine such as hexahistidine), myc or FLAG, and purifying the tag-polypeptide via affinity chromatography using, for example, a nickel column for polyhistidine, or a mono- or polyclonal antibody for myc or FLAG.

As mentioned above, the cdk portion of the cyclin E2/cdk2 holoenzyme must be phosphorylated at amino acid 160 in order for the holoenzyme to have kinase activity; phosphorylation of cdk amino acid 160 can only occur when cdk is associated with cyclin E2, thereby forming the holoenzyme. The cyclin E2/cdk complex can form spontaneously if the two polypeptides are co-expressed in eukaryotic or prokaryotic host cells. Further, when co-expressed in a eukaryotic host cell, the host cell's machinery can phosphorylate cdk amino acid 160, provided that the host cell has endogenous cyclin activating kinase ("cak"), which is responsible for such phosphorylation. The phosphorylated holoenzyme complex (the "active holoenzyme complex") can then be purified, typically using affinity chromatography.

One preferred method for producing the active holoenzyme complex is the baculovirus system such as the pFast-Bac DUAL® (Gibco/BRL Life Technologies, Grand Island, N.Y.). In this system, both the cdk and cyclin E2 genes can be expressed on the same vector, and the vector also contains a polyHis tag for ease of purification.

If the two polypeptides are produced in separate host cells of the same or different species, they can each be purified (preferably via affinity chromatography) and then combined in solution form the holoenzyme complex. ATP and cak (cyclin dependent activating kinase) can then be added to the holoenzyme complex; amino acid Threonine 160 of cdk can then be phosphorylated via cak, thereby generating an active holoenzyme complex. Once the active holoenzyme complex has been prepared and isolated, various in vitro assays for cyclin E2 inhibitors can be conducted.

In one such assay, the active holoenzyme complex is placed in solution. Gamma-labeled ATP (such as b 32P-ATP), holoenzyme substrate (such as histone Hi or retinoblastoma peptide), and the test molecule(s) can be added to the solution either simultaneously or successively. After a period of incubation, the substrate can be isolated and assayed for the amount of label it contains.

In one preferred assay, termed the "scintillation proximity assay", or "SPA" (Cook, *Drug Discovery Today,* 1:287–294 [1996]), biotinylated substrate (histone H1 or retinoblastoma peptide, for example) is attached to non-porous beads coated with streptavidin and filled with scintillation fluid. The beads can be incubated with active holoenzyme complex, gamma-labeled ATP, and the test molecule(s) using microtiter plates (such as 96 well plates or 384 well plates). When a radiolabeled phosphate group is transferred to the substrate via the kinase activity of the active holoenzyme complex, the photon released by the radioactive phosphate group is recorded by a scintillation counter. Those wells that contain test molecules which are effective in inhibiting cyclin E2 such that the kinase activity of the holoenzyme complex is disrupted will have fewer radioactive counts detected than control wells.

Other in vitro assays can also be conducted to evaluate test molecules. In one such assay, the substrate can be attached to wells of a microtiter plate, and active holoenzyme complex, gamma-labeled ATP (or other suitable detection agent), and the test molecule(s) can be added sequentially or simultaneously. After a short incubation (on the order of seconds to minutes), the solution can be removed from each well and the plates can be washed and then measured for the amount of labeled gamma phosphate added to the substrate by the activity of the holoenzyme complex.

Other variations on these assays will be apparent to the ordinary skilled artisan. For example, the substrate can be attached to beads as an alternative to attaching it to the bottom of each well; the beads can then be removed from solution after incubation with the test molecule, labeled ATP, and active holoenzyme complex, and measuring the amount of label incorporated in to the substrate.

Typically, in each type of assay, the test molecule will be evaluated over a range of concentrations, and a series of suitable controls can be used for accuracy in evaluating the results. In some cases, it may be useful to evaluate two or more test molecules together to assay for the possibility of "synergistic" effects.

B. In Vitro Assays Using Cultured Cells

Cultured eukaryotic cell lines that are actively dividing may be used to assay for the efficacy of a test molecule in inhibiting cyclin E2. Preferred cell lines are those such as mammalian Saos-2 cells (American Type Culture Collection, 10801 University Blvd., Manassas, Va., USA; accession number HTB-85) and human embryonic kidney 293T cells (American Type Culture Collection, accession number CRL-1573), which express detectable levels of cyclin E2, cdk, and cak. However, actively dividing cells into which the genes encoding cyclin E2 and/or cdk are transfected and expressed at a detectable level, but which express endogenous cak (or into which cak genes are also transfected and expressed) are also suitable for use in these assays.

Cell cultures can be exposed to the test molecule(s) for a predetermined amount of time (usually up to about 24 hours). The cells can be washed to remove remaining test molecule, and then measured for their ability to divide. Actively dividing cells can be identified in several ways. One preferred way is to incubate them for a short time in a compound such as bromo-deoxyuridine (BRDU), a nucleotide analog that is incorporated into DNA as it replicates; BRDU can be detected using a fluorescent-labeled antibody. Alternatively, or additionally, dividing cells can be detected using the Alamar Blue Assay (Biosource Intl., Camarillo, Calif.) Effective test molecules will be those which decrease the amount of cell division as compared to control assays.

While not intending to be bound to a particular mechanism of action, it is believed that inhibition of cyclin E2 may lead to cell death, or apoptosis. Therefore, cultured cells that have been exposed to one or more test molecules can also be evaluated for survival by use of trypan blue, or other dye or fluorescent molecule that is selectively excluded or taken up by live cells.

Other cell-based assays for detection of test molecule efficacy will readily be apparent to the ordinary skilled artisan.

The assays can be conducted using 96 well microtiter plates or other suitable plates that permit several assays to be conducted simultaneously. Typically, in each type of cell culture assay, the test molecule will be evaluated over a range of concentrations, and a series of "control wells" lacking either the test molecules, or the cultured cells, can be used for accuracy in evaluating the results. In some cases, it may be useful to evaluate two or more test molecules together to assay for the possibility of "synergistic" effects.

C. In Vivo Assays

Once test molecules have been identified, they can be evaluated for efficacy in rodent tumor models (see for example, O'Reilly et al., *Cell,* 88:277–285 [1997]). The test molecule can be administered prior to tumor onset in the rodent; after such administration, appearance of tumors can be monitored and compared against a control rodent not receiving the test molecule. Alternatively, the test molecule can be administered after onset of the tumor, and tumor size can be monitored.

The following examples are intended for illustration purposes only, and should not be construed as limiting the scope of the invention in any way.

EXAMPLES

1. Identification of Human Cyclin E2

An Amgen, Inc. internal EST ("expressed sequence tags") database, containing cDNAs from more than 200 different libraries, was searched using a peptide sequence designed to identify cyclin box-like domains.

A murine EST called BmmE7-133-G12 was obtained from this search, and was used to search the public database Genbank which contains human DNA sequences. One sequence, accession number R84331, was obtained. This sequence was used to design PCR primers to conduct a transcript survey.

The transcript survey was carried out by PCR using various Marathon® cDNA libraries (Clontech, Palo Alto, Calif.) with the following primers:

GAA GAG AAT GTC AAG ACG AAG AAG CC   (SEQ ID NO:10)

GCT TAA ATC AGG CAA AGG TGA AGG AT   (SEQ ID NO:11)

The conditions for the PCR were: 2.5 ul CDNA, 20 pmols of each primer, 0.5 ul 50× dNTPs, 0.5 ul AmpliTaq® enzyme (Perkin Elmer), 2.5 ul of 10× PCR buffer in a final volume of 25 ul. The cycle parameters were 94 C. for 2 minutes, followed by 35 cycles of 94 C. for 30 seconds, 60 C. for 30 seconds, 72 C. for 45 seconds, followed by 72 C. for 7 minutes after the last cycle. Fetal liver, fetal lung and thymus cDNAs were positive for cyclin transcript.

PCR of a Fetal Liver Marathon cDNA Library® (Clontech, Palo Alto, Calif.) was used to obtain the complete coding region of the cyclin E2 gene. The sense and antisense primers for this reaction were, respectively:

```
GAA GAG AAT GTC AAG ACG AAG AAG CC   (SEQ ID NO:10)

CCA TCC TAA TAC GAC TCA CTA TAG GGC  (SEQ ID NO:12)
```

The conditions for the PCR were: 2.5 ul cDNA, 5 pmols of each primer, 0.5 ul 50x dNTPs, 0.5 ul KlenTaq® polymerase (Clontech, Palo Alto, Calif.), 2.5 ul of 10x PCR buffer in a final volume of 25 ul. The cycle parameters were 94 C. for 1 minute followed by 35 cycles of 94 C. for30 seconds, followed by 68 C. for 3 minutes. PCR products were then run on a 1 percent agarose gel. A PCR product of approximately 2.58 kilo-base pairs (kb) was cut from the gel, and the gel slices were solubilized in sodium iodide and incubated at about 48 C. for about 1 hour. The DNA was then extracted and purified using the GeneClean® kit (Bio 101, Vista, Calif.) following the manufacturer's protocol, and ligated into the vector pCR2.1 (Invitrogen, Carlsbad, Calif.). This vector containing the insert was then transformed into *E. coli* Inv-alpha-f' cells (Invitrogen, Carlsbad, Calif.) for amplification. Plasmid was purified from the cells using the standard alkaline lysis method with the Qiagen Max1® kit (Qiagen, Santa Clarita, Calif.), and the insert was sequenced. Sequencing indicated that the insert contained the full length human cyclin E2 cDNA.

To confirm that the sequence obtained was correct, PCR was conducted using a high fidelity polymerase as follows. Fetal Lung and Thymus Marathon Libraries® (Clontech) were used as template, and the primers for this reaction were:

```
GAA GAG AAT GTC AAG ACG AAG AAG CC  (SEQ ID NO:10)

CAG TTC TAC CCA ATC TTG GTG AAT     (SEQ ID NO:13)
```

The conditions for the PCR were as follows; 2.5 ul cDNA, 5 pmols of each primer, 0.5 ul 50x dNTPs, 0.5 ul PFU polymerase (Stratagene, La Jolla, Calif.), 2.5 ul of 10x PCR buffer to a final volume of 25 ul. The cycle parameters were 94 C. for 2 minutes followed by 35 cycles of 94 C. for 30 seconds, 60 C. for 30 seconds, and 72 C. for 3 minutes. The resulting approximately 1.3 kb DNA band was resolved on an agarose gel and purified as descried above. The purified DNA product was subcloned into pCR2.1 as described above.

Digestion of 2 independent clones with the restriction enzyme EcoRI revealed one fragment of approximately 1.3 kb, and one fragment of approximately 1.2 kb. The sequence analysis of the two fragments revealed a full length cyclin E2 clone (the 1.3 kb fragment), and a cyclin E2 mutant clone (the 1.2 kb fragment) with an in-frame deletion of about 135 bp in the cyclin box lacking bases 496–631 of the full length clone.

The sequence of full length human cyclin E2 cDNA is set forth in FIG. 1 (SEQ ID NO:1), and the putative amino acid sequence, as translated from this cDNA, is set forth in FIG. 3 (SEQ ID NO:3). The cDNA sequence of the splice variant is set forth in FIG. 5 (SEQ ID NO:5), and the amino acid sequence of this splice variant is set forth in FIG. 6 (SEQ ID NO:6).

Analysis of this gene, and comparison with genes in the databases set forth above indicated that it was indeed a novel gene, with about 49 percent overall identity at both the DNA and amino acid sequence levels to human cyclin E1, and about 70 percent identity to the cyclin box domain of human cyclin E1 at the amino acid level. Due to the homology with cyclin E1, it was determined that this gene was a member of the cyclin family. Therefore, it was termed "cyclin E2".

The mutant cyclin E2 clone, which is an in-frame splice variant, lacks amino acids 166–212 (bases 496–631), which are located within the cyclin box. As described below in detail, this isoform does not bind cdk2.

A search of this human cyclin E2 cDNA sequence with the external, publicly available databases such as Genbank revealed an EST in the database that has homology to the 5' end of human cyclin E2 (Genbank accession number R84331) However, the Genbank sequence has several incorrect bases when compared to the same stretch of nucleotides in the present invention.

2. Cloning of Murine Cyclin E2.

The murine EST BmmE7-133-G12 described above was used to design the following PCR primers:

```
ATT TAA GCT GGG CAT GTT CAC AGG A   (SEQ ID NO:14)

GTC TTC AGC TTC ACT GGA CTC ACA CTT (SEQ ID NO:15)
```

A mouse brain Marathon Library® CDNA (Clontech, Palo Alto, Calif.) was used as the PCR template. The conditions for the PCR were as follows: 5 ul CDNA, 20 pmols of each primer, 0.5 ul 50x dNTPs, 0.5 ul AmpliTaq® (Roche Molecular Systems, Inc., Branchburg, N.J.), and 5 ul of 10x PCR buffer in a final volume of 50 ul. Reaction parameters were: 94 C. for 2 minutes followed by 35 cycles of 94 C. for 20 seconds, 60 C. for 30 seconds, 72 C. for 50 seconds, and a 72 C./ for 7 minutes hold after the last cycle. The PCR product was a fragment of about 723 bp, and contained residues 308 to 1031. This fragment was cloned into pCR2.1 (Invitrogen, Carlsbad, Calif.) and was transformed into *E. coli* cells as described above. After culturing the cells to amplify the plasmid, the plasmid was purified from the cells as described above, and the approximately 723 bp insert was digested with EcoRI which generated an approximately 153 bp fragment (residues 879 to 1031) and an approximately 570 bp (residues 308 to 878) fragment. The 570 bp fragment was gel purified using procedures described above, and was used as a DNA probe to screen a Uni-Zap® mouse testes XR library (Stratagene, La Jolla, Calif., catalog no. 937308). The library was plated out to approximately 1×10(6) PFUs (plaque forming units), and duplicate plaque lifts were prepared using charged nylon membranes (BioRad, Hercules, Calif.). The mouse cyclin E2 570 bp probe was radiolabeled using the Rediprimer® kit (Amersham Life Science, Arlington Heights, Ill.) following the manufactuere's protocol. The specific activity of the probe was about 1×10(9) cpm/microgram. Hybridization of the filters was conducted overnight at about 42 C. in standard hybridization solution containing 2.5× Denhardt's solution, 50 percent formamide, 0.1 percent SDS, 5× SSC, and 0.1 mg/ml salmon sperm DNA. After hybridization, the filters were washed twice in 2× SSC at room temperature for about 15 minutes, followed by three washes in 2× SSC at about 50 C. for about 30 minutes, and then once in 0.2× SSC plus 0.5 percent SDS at about 42 C. for 30 minutes. The filters were exposed to film at about minus 70 C. for about 3 days using intensifying screens.

Six positives were identified from this hybridization screen. The insert of each clone was subcloned into the vector pBluescript (Stratagene, La Jolla, Calif.) using standard techniques and each insert was sequenced.

The sequence of the murine cyclin E2 cDNA is set forth in FIG. 2 (SEQ ID NO:2). The putative amino acid sequence, as translated from the cDNA, is set forth in FIG. 4 (SEQ ID NO:4). Murine cyclin E2 had about 89 percent identity to human cyclin E2 at the DNA level, and about 92 percent identity to human cyclin E2 at the amino acid level.

3. Human Cyclin E2 Protein Preparation

Full length human cyclin E2 polypeptide was prepared as a glutathione-s-transferase fusion protein using the pGEX® system(Pharmacia, Piscataway, N.J.) and following the manufacturer's protocol. The cyclin E2 cDNA was inserted into the vector pGEX-4T-2 at the 3' end of the DNA encoding GST. The vector was transformed into $E$ $coli$ strain BL-21 cells (Invitrogen, San Diego, Calif.) that were transformation competent by mixing plasmid DNA with the cells. After culturing the cells overnight, the cells were diluted 1:100 in media and cultured for about 4 hours at 37 C., after which IPTG was added at a final concentration of 0.1 mM. After about 4 hours of culturing, protein extract was prepared from the cells using the GST Gene Fusion System® protocol (Pharmacia Biotech, Piscataway, N.J. following the manufacturer's protocol, and this extract was then added to a slurry of Glutathione-Agarose 4B Sepharose beads (Pharmacia Biotech, Piscataway, N.J.). The extract solution containing the beads was then centrifuged, and the beads were collected and washed. These beads were then mixed with a slurry of agarose beads to which thrombin protease was bound (Pharmacia Biotech, Piscataway, N.J.). After mixing and incubating the two sets of beads for about 1 hour at room temperature, the solution was centrifuged to pellet the beads. Samples of the supernatant were run on SDS-PAGE to assess purity. A photo of a Coomassie stained gel is shown in FIG. 9. As can be seen, only a single band of about 46 kDa was present; this band corresponds to the expected molecular weight for cyclin E2, indicating that the procedure resulted in generation of purified cyclin E2 polypeptide. To confirm that this band was indeed cyclin E2, a Western blot was prepared and probed with anti-cyclin E2 antiserum (using antiserum raised against the cyclin E2 peptide of SEQ ID NO:17).

4. Human Cyclin E2 Antibody Production

Rabbit polyclonal antiserum raised against two cyclin E2 peptides were prepared as follows. Peptides corresponding to the following two amino acid sequences were prepared using standard peptide synthesis procedures.

```
GQL SPV CNG GIM TPP KST EK   (SEQ ID NO:16)

AKQ QPQ PSQ TES PQE AQI IQA  (SEQ ID NO:17)
```

About 5 mg of each peptide was mixed with Freund's complete adjuvant in a total volume of about 1 ml, and injected subcutaneously into rabbits. After about 4 weeks, the rabbits were again injected with the same solution. After 2 weeks, the rabbits were bled and the serum was tested for antibodies to the peptides by Western blot. A third injection was administered after the test bleed, and about two weeks later, a second test bleed was conducted. About two weeks later, a fourth injection was administered, and about two weeks after that, the final blood collection was conducted.

Blood obtained from the final bleed was allowed to clot by incubating it at about 4 C. for about 2 hours. The serum was then obtained by centrifugation and collecting the supernatant. This serum was used for Western blots and immunoprecipitations described herein.

5. Human Cyclin E2 Expression in Mammalian Cells

Human full length cyclin E2 cDNA was inserted into the plasmid pEGFP-n1 (Invitrogen, San Diego, Calif.) which contains the coding region for green fluorescent protein ("GFP"). The cyclin E2 cDNA was inserted 3' to the GFP DNA to generate the vector pGFP-E2.

About 5 micrograms of plasmid was then transfected into about 2×10(6) human embryonic kidney 293T cells using the standard calcium phosphate transfection procedure.

Simultaneously, the cells were transfected with a vector, called HA-cdk2, containing the gene encoding human cdk2 (Turner et al., $Genes$ $and$ $Devel.,$ 8:1434–1447 [1994]).

After transfection, the cells were incubated at about 37 C. for about 24 hours, after which the cells were harvested into about 200 microliters of a buffer termed "TG buffer" containing 1 percent Triton X-100, 10 percent glycerol, 0.1 percent SDS, 0.5 percent deoxycholate, 20 mM Hepes pH 7.4, 100 mM NaCl, and about 1 mM each of leupeptin, aprotinin, PMSF, sodium vanadate, and sodium fluoride. Cell debris was removed by centrifugation at about 10,000× g, after which the supernatant was collected and the pellet discarded.

To the extract was added about 1 microliter of anti-GFP polyclonal antiserum (Invitrogen, San Diego, Calif.) and the extract was incubated at about 4 C. for about 1 hour. After incubation, about 50 microliters of Protein A/Protein G agarose beads (Pierce Biochemicals, Rockford, Ill.) was added, and the mixture was incubated about 30 minutes at about 4 C. After this incubation, the beads were pelleted and washed five times with TG buffer minus SDS and deoxycholate. After washing, the beads were resuspended in standard SDS-PAGE sample buffer, heated at about 95 C. for about 3 minutes, centrifuged, and the supernatant was collected and loaded on to a 12 percent SDS-PAGE gel.

The gel was transferred to PVDF membrane (NEN Life Sciences, Burton, Mass.) using standard Western blotting procedures, and the membrane was cut into strips for probing with different antibodies including anti-GFP (Invitrogen, San Diego, Calif.), anti-HA (Beohringer-Mannheim, Indianapolis, Ind.), and anti-p27 (Santa Cruz Biologicals, Santa Cruz, Calif.).

Separately, the same procedure was followed for the human cyclin E2 splice variant, and the same procedures as those described immediately above for the wild type cyclin E2 transfected cells were conducted for these cells in order to determine whether cdk binds to the splice variant.

In one other separate set of experiments, a DNA construct containing a cDNA encoding human p27 (Polyak et al., $Cell,$ 78:59–66 [1994]) was co-transfected to cells that were also transfected with full length cyclin E2 and cdk2. The procedures followed for this transfection were the same as those set forth above.

The results of Western blot analysis are shown in FIG. 10A–D. As shown in 10A, GFP protein fused to either full length cyclin E2 or the splice variant "sv" cyclin E2 is immunoprecipitated using anti-GFP antiserum. IgG heavy chain is also detected in the Western blot as indicated. FIG. 10B shows that GFP alone is also immunoprecipitated by the anti-GFP antiserum. FIG. 10C shows that cdk2 associates (and thus co-immunoprecipitates) with wild type cyclin E2 but not with the cyclin E2 splice variant, and therefore, the middle portion of the cyclin box domain, which is missing in the splice variant, is likely responsible for cdk2 binding to cyclin E2. FIG. 10D shows that in a three way transfection of the cells with cdk2, cyclin E2 (full length) and p27 DNA constructs, p27 co-immunoprecipitates with the other two proteins, indicating that p27 forms a complex with cdk2 and cyclin E2. FIG. 10E shows that a complex containing full length cyclin E2 and cdk2 can phosphorylate histone H1, and that the presence of p27 decreases the amount of phosphorylation. In addition, the cyclin E2 splice variant-cdk2 complex cannot phosphorylate histone H1. The experiments for this kinase assay were conducted as described immediately below.

6. Biological Activity of Cyclin E2

Figure 15A:
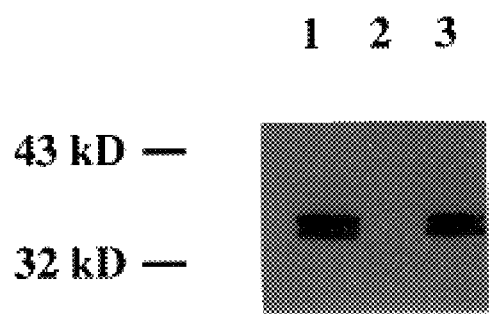
FIGS. 15A and 15B depict a Western blot (15A) and an kinase assay (15B) of a human osteosarcoma derived cell line termed Saos-2. In 15A, cells were lysed and immunoprecipitated with either pre-immune ("PI"; Lane 2) or with anti-cyclin E2 antiserum ("E2"; Lane 3). The immunoprecipitates were run on SDS-PAGE from which a Western blot was generated. The blot was probed with an anti-cdk2 antibody. In 15B, extract was prepared from the same cell line and was treated with anticyclin E2 antibody (Lanes 2–4) or preimmune serum (Lane 14), GST-Rb protein (Lane 3), or histone H1 protein (Lane 2) was then added to the immunoprecipitate. After 30 minutes at 37° C., the immunoprecipitates were run on SDS-PAGE, and exposed to film for 2 hours.
Figure 15B:
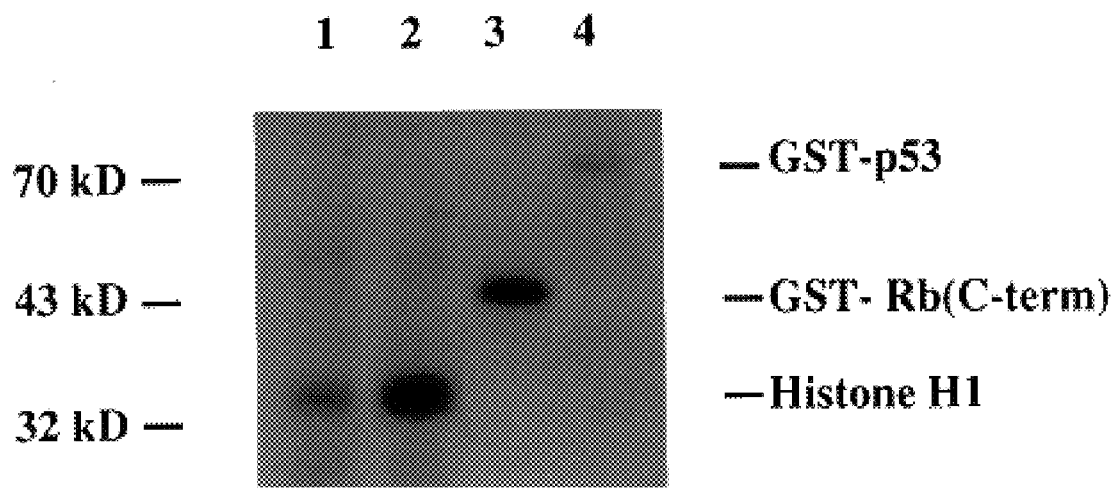

Biological activity of cyclin E2/cdk2 was evaluated using a kinase assay. Extracts were prepared by treating about 2×10 (6) Saos-2 cells (American Type Culture Collection, 10801 University Blvd., Manassas, Va., USA) with about 200 microliters of TG buffer (see above), and centrifuging the extract to pellet cellular debris. About 3 microliters of antibody (either anti cyclin E2 raised against the peptide of SEQ ID NO:17, anti-GFP, or preimmune serum "PI") was added to about 500 micrograms of cell extract protein, and the mixture was incubated about 1 hour at about 4 C. About 50 microliters of Protein A/G Sepharose beads was then added, and this mixture was incubated about 30 minutes at about 4 C. The beads were then washed about 4 times with TG buffer (about 500 microliters per wash) after which kinase buffer containing 50 mM Tris pH 7.5, 10 mM MgCl2, 1 mM DTT, 25 mM ATP, and 40 micro-CI of gamma-32P-ATP was added to the extract. Various potential kinase substrates were then added, including histone H1, GST-retinoblastoma ( pRb; Santa Cruz Biotechnology, Santa Cruz, Calif.), or GSTp53 (Santa Cruz Biotechnology). The mixture was then incubated at about 37 C. for about 30 minutes, after which standard 2× SDS-PAGE sample buffer was added. The samples were heated at about 95 C. for about 3 minutes, run on SDS-PAGE, and exposed to film for 2 hours. The results can be seen in FIG. 15, Panel B. As is apparent, the cyclin E2-cdk2 complex can phosphorylate GST-Rb and Histone H1, but not GST-p53.

7. Tissue Specific Expression of Cyclin E2

Northern blot analysis was used to identify those tissues in which cyclin E2 is expressed. A Northern blot containing about 2 micrograms of poly A+ RNA from various human tissues was purchased (Clontech, Palo Alto, Calif.) and was probed with either an approximately 320 bp human cyclin E2 CDNA fragment spanning a region 5' to the cyclin box, a 310 base pair cyclin E1 fragment spanning amino acids 272–377 of human cyclin E1, or a human GADPH (glyceraldehyde-phospho-dehydrogenase) probe of about 550 bp encoding a portion of the human GADPH gene. The probes were labeled using the RediPrimer® kit (Amersham, Arlington Heights, Ill.), and the final activity of the labeled probes was about 1×10(9) cpm per microgram. The blots were prehybridized about 2 hours, and hybridized overnight at about 42 C. in a hybridization solution containing 2× Denhardt's, 0.5 percent SDS, 50 percent formamide, 0.1 mg per microgram of salmon sperm DNA, and 5× SSC. The specific activity of the probe in this solution was about 2×10(6) cpm. After hybridization, the blots were washed three times in 2× SSC containing 0.1 percent SDS at room temperature, twice in 2× SSC containing 0.1 percent SDS at 50 C., and once in 0.1× SSC containing 0.5 percent SDS at 50 C. Films were exposed at about minus 70 C. for two days. The resulting autorads were scanned into a computer, and the data was converted to a bar graph to quantitate the relative amounts of RNA detected by each probe.

The results are shown in FIG. 12, and the human tissues analyzed are indicated on the x-axis. As can be seen, testes tissue had the highest level of both cyclin E2 and cyclin E1 RNA. Cyclin E1 RNA was present in peripheral blood lymphocytes ("PBL"), but cyclin E2 RNA was not. Cyclin E2 RNA was present in spleen and thymus, but cyclin E1 RNA was not.

To assess cyclin E2 RNA levels in tumor tissues, several breast cancer cell lines, together with normal immortalized breast tissue cell lines, were evaluated. The cell lines are listed in FIG. 13. All cell lines are available from the American Type Culture Collection.

The NMEC, 184A1 and MCF10 cells were cultured in modified DME/F12 (Gibco/BRL, Grand Island, N.Y.) medium supplemented with 10 mM Hepes, 2 mM glutamine, 0.1 mM non-essential amino acids, 0.5 mM ethanolamine, 5 micrograms/ml transferrin, 1 mg/ml bovine serum albumin, 5.0 ng/ml sodium selenite, 20 ng/ml triiodothyronine, 10 ng/ml EGF, 5 micrograms/ml insulin, and 0.5 micrograms/ml hydrocortisone. Bovine pituitary extract (30 micrograms/ml) was also added to the medium for the NMEC cell lines. The ER+ and ER– (estrogen receptor positive and negative) breast cancer cell lines were cultured in alpha or Richter improved minimal essential medium (Gibco/BRL, Grand Island, N.Y.) supplemented with 10 mM Hepes, 2 mM glutamine, 0.1 mM non-essential amino acids, 10 percent fetal bovine serum, and 1 microgram/ml insulin. All cells were routinely screened for mycoplasma contamination, and were maintained at 37 C. in an atmosphere of about 6.5 percent carbon dioxide.

Total RNA was prepared from each cell line by lysing cell monolayers in guanidinium isothiocyanate and centrifuging over a cesium chloride cushion as described by Gudas et al. (*Proc. Natl. Acad. Sci USA,* 85:4705–4709 [1988]). About 20 micrograms of RNA was electrophoresed on denaturing formaldehyde gels, transferred to Magna NT membranes (Micron Separations Inc., Westboro, Mass.), and cross linked with UV radiation. The probes for Northern blot analysis included the full length cyclin E1 cDNA, and an approximately 330 bp fragment of cyclin E2 (as described above). The probes were labeled with 32P-dCTP to a specific activity of about 1×10(9) cpm/microgram DNA using a random-primed labeling kit (Boehringer-Mannheim, Indianapolis, Ind.). The blot was hybridized in a solution containing 50 percent formamide, 0.2 percent SDS, 6× SSPE, 2× Denhardt's and 100 ng/ml salmon sperm DNA. Hybridization was conducted at about 41 C. for about 24 hours, after which the blot was washed once in 2× SSC containing 0.5 percent SDS at room temperature; once in 0.5× SSC containing 0.5 percent SDS at room temperature; once in 0.2× SSC containing 0.5 percent SDS at room temperature; and three times in 0.5× SSC containing 0.5 percent SDS at about 59 C.

The results of Northern analysis are shown in FIG. 13. As can be seen, cyclin E2 RNA is present in some ER+ and some ER– cell lines, but is hardly detectable in normal cells. Cyclin E1 RNA is present in fewer breast cancer cell lines as compared to cyclin E2.

We claim:

1. A cyclin E2 polypeptide selected from the group consisting of:

(a) the polypeptide of SEQ ID NO:3;

(b) the polypeptide of SEQ ID NO:4;

(c) the polypeptide of SEQ ID NO:6; and (d) a polypeptide that is at least 70 percent identical to any of the polypeptides of (a)–(c).

2. The cyclin E2 polypeptide of claim 1 that does not possess an amino terminal methionine.

3. An isolated polypeptide of SEQ ID NO:3.

4. An isolated polypeptide of SEQ ID NO:4.

5. An isolated polypeptide of SEQ ID NO:6.

* * * * *

UNITED STATES PATENT AND TRADEMARK OFFICE
CERTIFICATE OF CORRECTION

PATENT NO. : 5,973,119
DATED : October 26, 1999
INVENTOR(S) : Coats, et al.

It is certified that error appears in the above-identified patent and that said Letters Patent is hereby corrected as shown below:

Column 3, line 20: Insert -- Other -- between the words "body." and "related" and make this last sentence a paragraph.

Column 9, line 42: Insert --elements-- between the words "regulation" and "as" and "as".

Column 20, line 16: Change "assoicated" to -- associated --.

Column 23, line 5: Remove the letter "b" between "as" and "32P-ATP".

Column 25, line 50: Change "descried" to -- described --.

Signed and Sealed this

Twenty-ninth Day of August, 2000

Attest:

Q. TODD DICKINSON

*Attesting Officer*     *Director of Patents and Trademarks*

SEQUENCE LISTING

<160> NUMBER OF SEQ ID NOS: 18

<210> SEQ ID NO 1
<211> LENGTH: 1215
<212> TYPE: DNA
<213> ORGANISM: Human

<400> SEQUENCE: 1

| | | | | | |
|---|---|---|---|---|---|
| atgtcaagac | gaagtagccg | tttacaagct | aagcagcagc | cccagcccag | ccagacggaa | 60 |
| tccccccaag | aagcccagat | aatccaggcc | aagaagagga | aaactaccca | ggatgtcaaa | 120 |
| aaaagaagag | aggaggtcac | caagaaacat | cagtatgaaa | ttaggaattg | ttggccacct | 180 |
| gtattatctg | gggggatcag | tccttgcatt | atcattgaaa | cacctcacaa | agaaatagga | 240 |
| acaagtgatt | tctccagatt | tacaaattac | agatttaaaa | atcttttat | taatccttca | 300 |
| cctttgcctg | atttaagctg | gggatgttca | aaagaagtct | ggctaaacat | gttaaaaaag | 360 |
| gagagcagat | atgttcatga | caaacatttt | gaagttctgc | attctgactt | ggaaccacag | 420 |
| atgaggtcca | tacttctaga | ctggcttta | gaggtatgtg | aagtatacac | acttcatagg | 480 |
| gaaacatttt | atcttgcaca | agacttttt | gatagattta | tgttgacaca | aaaggatata | 540 |
| aataaaaata | tgcttcaact | cattggaatt | acctcattat | tcattgcttc | caaacttgag | 600 |
| gaaatctatg | ctcctaaact | ccaagagttt | gcttacgtca | ctgatggtgc | ttgcagtgaa | 660 |
| gaggatatct | taaggatgga | actcattata | ttaaaggctt | taaatgggaa | actttgtcct | 720 |
| gtaacaatca | tctcctggct | aaatctcttt | ctccaagttg | atgctcttaa | agatgctcct | 780 |
| aaagttcttc | tacctcagta | ttctcaggaa | acattcattc | aaatagctca | gcttttagat | 840 |
| ctgtgtattc | tagccattga | ttcattagag | ttccagtaca | gaatactgac | tgctgctgcc | 900 |
| ttgtgccatt | ttacctccat | tgaagtggtt | aagaaagcct | caggtttgga | gtgggacagt | 960 |
| atttcagaat | gtgtagattg | gatggtacct | tttgtcaatg | tagtaaaaag | tactagtcca | 1020 |
| gtgaagctga | agacttttaa | gaagattcct | atggaagaca | gacataatat | ccagacacat | 1080 |
| acaaactatt | tggctatgct | ggaggaagta | aattacataa | acaccttcag | aaaaggggga | 1140 |
| cagttgtcac | cagtgtgcaa | tggaggcatt | atgacaccac | cgaagagcac | tgaaaaacca | 1200 |
| ccaggaaaac | actaa | | | | | 1215 |

<210> SEQ ID NO 2
<211> LENGTH: 1212
<212> TYPE: DNA
<213> ORGANISM: Mouse

<400> SEQUENCE: 2

| | | | | | |
|---|---|---|---|---|---|
| atgtcaagac | gcagccgttt | acaagctaag | caacatgccc | agcccaacca | gccagactct | 60 |
| ccgcaagaaa | cccagataat | tcaggccaag | aagagaaaaa | cagcacagga | tgtcaaaaaa | 120 |
| agaaaagagg | agatcaccaa | gaagcatcag | tatgagatta | ggaattgttg | gccacctgta | 180 |
| ctgtctggag | gaatcagccc | ttgcattatc | attgaaacac | cccataaaga | aataggaaca | 240 |
| agtgacttct | ctagatttac | aaattacaga | tttaaaaatc | ttttattaa | tccctcacct | 300 |
| ctgccagatt | taagctgggc | atgttcacag | gaggtttggc | aaaacatgtt | acaaaaggaa | 360 |
| aacagatacg | tgcatgacaa | acattttcaa | gttctgcatt | ctgacctgga | accacagatg | 420 |
| aggtcaatac | ttttagactg | gctttagag | gtttgtgaag | tatacactct | tcatagggag | 480 |
| acattttacc | ttgcccaaga | ctttttgac | agatttatgt | tgacacaaaa | ggatgtaaat | 540 |

-continued

```
aaaaatatgc ttcaactcat tgggattacc tcattgttca ttgcttccaa acttgaggaa      600
atctacgctc ctaaactcca agagtttgct tacgtcactg atggtgcttg cagtgaagta      660
gatatcttaa agatggaact caatatatta aaggctttaa aatgggaact ttgtccagta      720
acagtcatct cctggttgaa tcttttcctt caagttgatg ctgttaaaga tgttcctaag      780
gttcttctac ctcaatattc tcaggagacg ttcatccaga tagctcagct tttagatctg      840
tgcattctag ccatcgactc tttagaattt caatacagaa ttctggctgc tgccgcctta      900
tgtcatttta cctccattga agtggttaag aaagcttcag gtttggaatg ggatgacatc      960
tcggaatgtg tagactggat ggtgcctttt gttagtgttg taaaaagtgt gagtccagtg     1020
aagctgaaga cttttaagaa gatacccatg gaagatagac acaatatcca gacacacaca     1080
aattatttgg ctttgctgaa tgaagtaaac tatgtgaaca tctacagaaa aggagggcag     1140
ctgtcaccag tgtgtaatgg aggcattatg acaccaccaa agagtactga aaaaccacca     1200
ggaaaacact ga                                                         1212
```

<210> SEQ ID NO 3
<211> LENGTH: 404
<212> TYPE: PRT
<213> ORGANISM: Human

<400> SEQUENCE: 3

```
Met Ser Arg Arg Ser Arg Leu Gln Ala Lys Gln Gln Pro Gln Pro
  1               5                  10                  15

Ser Gln Thr Glu Ser Pro Gln Glu Ala Gln Ile Ile Gln Ala Lys Lys
                 20                  25                  30

Arg Lys Thr Thr Gln Asp Val Lys Lys Arg Arg Glu Glu Val Thr Lys
             35                  40                  45

Lys His Gln Tyr Glu Ile Arg Asn Cys Trp Pro Pro Val Leu Ser Gly
         50                  55                  60

Gly Ile Ser Pro Cys Ile Ile Ile Glu Thr Pro His Lys Glu Ile Gly
 65                  70                  75                  80

Thr Ser Asp Phe Ser Arg Phe Thr Asn Tyr Arg Phe Lys Asn Leu Phe
                 85                  90                  95

Ile Asn Pro Ser Pro Leu Pro Asp Leu Ser Trp Gly Cys Ser Lys Glu
                100                 105                 110

Val Trp Leu Asn Met Leu Lys Lys Glu Ser Arg Tyr Val His Asp Lys
            115                 120                 125

His Phe Glu Val Leu His Ser Asp Leu Glu Pro Gln Met Arg Ser Ile
        130                 135                 140

Leu Leu Asp Trp Leu Leu Glu Val Cys Glu Val Tyr Thr Leu His Arg
145                 150                 155                 160

Glu Thr Phe Tyr Leu Ala Gln Asp Phe Phe Asp Arg Phe Met Leu Thr
                165                 170                 175

Gln Lys Asp Ile Asn Lys Asn Met Leu Gln Leu Ile Gly Ile Thr Ser
            180                 185                 190

Leu Phe Ile Ala Ser Lys Leu Glu Glu Ile Tyr Ala Pro Lys Leu Gln
        195                 200                 205

Glu Phe Ala Tyr Val Thr Asp Gly Ala Cys Ser Glu Glu Asp Ile Leu
    210                 215                 220

Arg Met Glu Leu Ile Ile Leu Lys Ala Leu Lys Trp Glu Leu Cys Pro
225                 230                 235                 240

Val Thr Ile Ile Ser Trp Leu Asn Leu Phe Leu Gln Val Asp Ala Leu
                245                 250                 255
```

-continued

```
Lys Asp Ala Pro Lys Val Leu Leu Pro Gln Tyr Ser Gln Glu Thr Phe
            260                 265                 270

Ile Gln Ile Ala Gln Leu Leu Asp Leu Cys Ile Leu Ala Ile Asp Ser
        275                 280                 285

Leu Glu Phe Gln Tyr Arg Ile Leu Thr Ala Ala Ala Leu Cys His Phe
    290                 295                 300

Thr Ser Ile Glu Val Val Lys Lys Ala Ser Gly Leu Glu Trp Asp Ser
305                 310                 315                 320

Ile Ser Glu Cys Val Asp Trp Met Val Pro Phe Val Asn Val Lys
            325                 330                 335

Ser Thr Ser Pro Val Lys Leu Lys Thr Phe Lys Lys Ile Pro Met Glu
        340                 345                 350

Asp Arg His Asn Ile Gln Thr His Thr Asn Tyr Leu Ala Met Leu Glu
    355                 360                 365

Glu Val Asn Tyr Ile Asn Thr Phe Arg Lys Gly Gln Leu Ser Pro
370                 375                 380

Val Cys Asn Gly Gly Ile Met Thr Pro Pro Lys Ser Thr Glu Lys Pro
385                 390                 395                 400

Pro Gly Lys His

<210> SEQ ID NO 4
<211> LENGTH: 403
<212> TYPE: PRT
<213> ORGANISM: Mouse

<400> SEQUENCE: 4

Met Ser Arg Arg Ser Arg Leu Gln Ala Lys Gln His Ala Gln Pro Asn
1               5                   10                  15

Gln Pro Asp Ser Pro Gln Glu Thr Gln Ile Ile Gln Ala Lys Lys Arg
            20                  25                  30

Lys Thr Ala Gln Asp Val Lys Lys Arg Lys Glu Ile Thr Lys Lys
        35                  40                  45

His Gln Tyr Glu Ile Arg Asn Cys Trp Pro Pro Val Leu Ser Gly Gly
    50                  55                  60

Ile Ser Pro Cys Ile Ile Glu Thr Pro His Lys Glu Ile Gly Thr
65                  70                  75                  80

Ser Asp Phe Ser Arg Phe Thr Asn Tyr Arg Phe Lys Asn Leu Phe Ile
                85                  90                  95

Asn Pro Ser Pro Leu Pro Asp Leu Ser Trp Ala Cys Ser Gln Glu Val
            100                 105                 110

Trp Gln Asn Met Leu Gln Lys Glu Asn Arg Tyr Val His Asp Lys His
        115                 120                 125

Phe Gln Val Leu His Ser Asp Leu Glu Pro Gln Met Arg Ser Ile Leu
    130                 135                 140

Leu Asp Trp Leu Leu Glu Val Cys Glu Val Tyr Thr Leu His Arg Glu
145                 150                 155                 160

Thr Phe Tyr Leu Ala Gln Asp Phe Phe Asp Arg Phe Met Leu Thr Gln
                165                 170                 175

Lys Asp Val Asn Lys Asn Met Leu Gln Leu Ile Gly Ile Thr Ser Leu
            180                 185                 190

Phe Ile Ala Ser Lys Leu Glu Glu Ile Tyr Ala Pro Lys Leu Gln Glu
        195                 200                 205

Phe Ala Tyr Val Thr Asp Gly Ala Cys Ser Glu Val Asp Ile Leu Lys
    210                 215                 220

Met Glu Leu Asn Ile Leu Lys Ala Leu Lys Trp Glu Leu Cys Pro Val
```

```
            225                 230                 235                 240
Thr Val Ile Ser Trp Leu Asn Leu Phe Leu Gln Val Asp Ala Val Lys
            245                 250                 255
Asp Val Pro Lys Val Leu Leu Pro Gln Tyr Ser Gln Glu Thr Phe Ile
            260                 265                 270
Gln Ile Ala Gln Leu Leu Asp Leu Cys Ile Leu Ala Ile Asp Ser Leu
            275                 280                 285
Glu Phe Gln Tyr Arg Ile Leu Ala Ala Ala Leu Cys His Phe Thr
            290                 295                 300
Ser Ile Glu Val Val Lys Lys Ala Ser Gly Leu Glu Trp Asp Asp Ile
305                 310                 315                 320
Ser Glu Cys Val Asp Trp Met Val Pro Phe Val Ser Val Lys Ser
                325                 330                 335
Val Ser Pro Val Lys Leu Lys Thr Phe Lys Lys Ile Pro Met Glu Asp
            340                 345                 350
Arg His Asn Ile Gln Thr His Thr Asn Tyr Leu Ala Leu Leu Asn Glu
            355                 360                 365
Val Asn Tyr Val Asn Ile Tyr Arg Lys Gly Gln Leu Ser Pro Val
            370                 375                 380
Cys Asn Gly Gly Ile Met Thr Pro Pro Lys Ser Thr Glu Lys Pro Pro
385                 390                 395                 400
Gly Lys His

<210> SEQ ID NO 5
<211> LENGTH: 1080
<212> TYPE: DNA
<213> ORGANISM: Human

<400> SEQUENCE: 5
atgtcaagac gaagtagccg tttacaagct aagcagcagc cccagcccag ccagacggaa      60
tccccccaag aagcccagat aatccaggcc aagaagagga aaactaccca ggatgtcaaa     120
aaaagaagag aggaggtcac caagaaacat cagtatgaaa ttaggaattg ttggccacct     180
gtattatctg gggggatcag tccttgcatt atcattgaaa cacctcacaa agaaatagga     240
acaagtgatt tctccagatt tacaaattac agatttaaaa atcttttttat taatccttca     300
cctttgcctg atttaagctg gggatgttca aaagaagtct ggctaaacat gttaaaaaag     360
gagagcagat atgttcatga caaacatttt gaagttctgc attctgactt ggaaccacag     420
atgaggtcca tacttctaga ctggcttta gaggtatgtg aagtatacac acttcatagg     480
gaaacatttt atcttgctta cgtcactgat ggtgcttgca gtgaagagga tatcttaagg     540
atggaactca ttatattaaa ggctttaaaa tgggaacttt gtcctgtaac aatcatctcc     600
tggctaaatc tctttctcca agttgatgct cttaaagatg ctcctaaagt tcttctacct     660
cagtattctc aggaaacatt cattcaaata gctcagcttt tagatctgtg tattctagcc     720
attgattcat tagagttcca gtacagaata ctgactgctg ctgccttgtg ccatttttacc     780
tccattgaag tggttaagaa agcctcaggt ttggagtggg acagtatttc agaatgtgta     840
gattggatgg tacctttttgt caatgtagta aaaagtacta gtccagtgaa gctgaagact     900
tttaagaaga ttcctatgga agacagacat aatatccaga cacatacaaa ctatttggct     960
atgctggagg aagtaaatta cataaacacc ttcagaaaag ggggacagtt gtcaccagtg    1020
tgcaatggag gcattatgac accaccgaag agcactgaaa aaccaccagg aaaacactaa    1080

<210> SEQ ID NO 6
```

```
<211> LENGTH: 359
<212> TYPE: PRT
<213> ORGANISM: Human

<400> SEQUENCE: 6

Met Ser Arg Arg Ser Ser Arg Leu Gln Ala Lys Gln Gln Pro Gln Pro
 1               5                  10                  15

Ser Gln Thr Glu Ser Pro Gln Glu Ala Gln Ile Ile Gln Ala Lys Lys
            20                  25                  30

Arg Lys Thr Thr Gln Asp Val Lys Lys Arg Arg Glu Glu Val Thr Lys
        35                  40                  45

Lys His Gln Tyr Glu Ile Arg Asn Cys Trp Pro Pro Val Leu Ser Gly
    50                  55                  60

Gly Ile Ser Pro Cys Ile Ile Glu Thr Pro His Lys Glu Ile Gly
 65                  70                  75                  80

Thr Ser Asp Phe Ser Arg Phe Thr Asn Tyr Arg Phe Lys Asn Leu Phe
                85                  90                  95

Ile Asn Pro Ser Pro Leu Pro Asp Leu Ser Trp Gly Cys Ser Lys Glu
            100                 105                 110

Val Trp Leu Asn Met Leu Lys Lys Glu Ser Arg Tyr Val His Asp Lys
        115                 120                 125

His Phe Glu Val Leu His Ser Asp Leu Glu Pro Gln Met Arg Ser Ile
    130                 135                 140

Leu Leu Asp Trp Leu Leu Glu Val Cys Glu Val Tyr Thr Leu His Arg
145                 150                 155                 160

Glu Thr Phe Tyr Leu Ala Tyr Val Thr Asp Gly Ala Cys Ser Glu Glu
                165                 170                 175

Asp Ile Leu Arg Met Glu Leu Ile Ile Leu Lys Ala Leu Lys Trp Glu
            180                 185                 190

Leu Cys Pro Val Thr Ile Ile Ser Trp Leu Asn Leu Phe Leu Gln Val
        195                 200                 205

Asp Ala Leu Lys Asp Ala Pro Lys Val Leu Leu Pro Gln Tyr Ser Gln
    210                 215                 220

Glu Thr Phe Ile Gln Ile Ala Gln Leu Leu Asp Leu Cys Ile Leu Ala
225                 230                 235                 240

Ile Asp Ser Leu Glu Phe Gln Tyr Arg Ile Leu Thr Ala Ala Ala Leu
                245                 250                 255

Cys His Phe Thr Ser Ile Glu Val Val Lys Lys Ala Ser Gly Leu Glu
            260                 265                 270

Trp Asp Ser Ile Ser Glu Cys Val Asp Trp Met Val Pro Phe Val Asn
        275                 280                 285

Val Val Lys Ser Thr Ser Pro Val Lys Leu Lys Thr Phe Lys Lys Ile
    290                 295                 300

Pro Met Glu Asp Arg His Asn Ile Gln Thr His Thr Asn Tyr Leu Ala
305                 310                 315                 320

Met Leu Glu Glu Val Asn Tyr Ile Asn Thr Phe Arg Lys Gly Gly Gln
                325                 330                 335

Leu Ser Pro Val Cys Asn Gly Gly Ile Met Thr Pro Pro Lys Ser Thr
            340                 345                 350

Glu Lys Pro Pro Gly Lys His
        355

<210> SEQ ID NO 7
<211> LENGTH: 1214
<212> TYPE: RNA
<213> ORGANISM: Human
```

-continued

<400> SEQUENCE: 7

```
auguccoguc guuccucccg ucugcaggcu aaacagcagc cgcagccguc ccagaccgaa     60
uccccgcagg aagcucagau cauccaggcu aaaaaacgua aaaccaccca ggacguuaaa    120
aaacgucgug aagaaguuac caaaaaacac caguacgaaa uccguaacug cuggccgccg    180
guucuguccg gugguaucuc cccgugcauc aucaucgaaa ccccgcacaa agaaaucggu    240
accuccgacu ucucccguuu caccaacuac cguuucaaaa accuguucau caacccgucc    300
ccgcugccgg accuguccug ggguugcucc aaagaaguuu ggcugaacau gcugaaaaaa    360
gaaucccguu acguucacga caaacacuuc gaaguucugc acuccgaccu ggaaccgcag    420
augcguucca uccugcugga cuggcugcug gaaguuugcg aaguuuacac ccugcaccgu    480
gaaaccuucu accuggcuca ggacuucuuc gaccguuuca ugcugaccca gaaagacauc    540
aacaaaaaca ugcugcagcu gaucgguauc accucccugu ucaucgcuuc caaacuggaa    600
gaaaucuacg cuccgaaacu gcaggaauuc gcuuacguua ccgacggugc uugcuccgaa    660
gaagacaucc ugcguaugga acugaucauc cugaaagcuc ugaaauggga acugugcccg    720
guuaccauca ucuccuggcu gaaccuguuc cugcagguug acgcucugaa agacgcuccg    780
aaaguucugc ugccgcagua cucccaggaa accuucaucc agaucgcuca gcugcuggac    840
cugugcaucc uggcuaucga cucccuggaa uuccaguacc guauccugac cgcugcugcu    900
cugugccacu ucaccuccau cgaaguuguu aaaaaagcuu ccggucugga augggacucc    960
aucuccgaau gcguugacug gaugguuccg uucguuaacg uuguuaaauc caccuccccg   1020
guuaaacuga aaaccuucaa aaaaaucccg auggaagacc gucacaacau ccagacccac   1080
accaacuacc uggcuaugcu ggaagaaguu aacuacauca acaccuuccg uaaaggugu    1140
cagcuguccc cgguuugcaa cggugguauc augaccccgc cgaaauccac cgaaaaaccg   1200
ccgguaaac acug                                                      1214
```

<210> SEQ ID NO 8
<211> LENGTH: 1215
<212> TYPE: DNA
<213> ORGANISM: Human

<400> SEQUENCE: 8

```
atgwsnmgnm gnwsnwsnmg nytncargcn aarcarcarc cncarccnws ncaracngar     60
wsnccncarg argcncarat hathcargcn aararmgna aracnacnca rgaygtnaar    120
aarmgnmgng argargtnac naaraarcay cartaygara thmgnaaytg ytggccnccn    180
gtnytnwsng gnggnathws nccntgyath athathgara cnccncayaa rgarathggn    240
acnwsngayt tywsnmgntt yacnaaytay mgnttyaara ayytnttyat haayccnwsn    300
ccnytnccng ayytnwsntg gggntgywsn aargargtnt ggytnaayat gytnaaraar    360
garwsnmgnt aygtncayga yaarcaytty gargtnytnc aywsngayyt ngarccncar    420
atgmgnwsna thytnytnga ytggytnytn gargtntgyg argtntayac nytncaymgn    480
garacnttyt ayytngcnca rgayttytty gaymgnttya tgytnacnca raargayath    540
aayaaraaya tgytncaryt nathggnath acnwsnytnt tyathgcnws naarytngar    600
garathtayg cnccnaaryt ncargartty gcntaygtna cngayggngc ntgywsngar    660
gargayathy tnmgnatgga rytnathath ytnaargcny tnaartggga rytntgyccn    720
gtnacnatha thwsntggyt naayytntty ytncargtng aygcnytnaa rgaygcnccn    780
aargtnytny tnccncarta ywsncargar acnttyathc arathgcnca rytnytngay    840
```

-continued ytntgyathy tngcnathga ywsnytngar ttycartaym gnathytnac ngcngcngcn 900
ytntgycayt tyacnwsnat hgargtngtn aaraargcnw snggnytnga rtgggaywsn 960
athwsngart gygtngaytg gatggtnccn ttygtnaayg tngtnaarws nacnwsnccn 1020
gtnaarytna aracnttyaa raarathccn atggargaym gncayaayat hcaracncay 1080
acnaaytayy tngcnatgyt ngargargtn aaytayatha ayacnttymg naarggnggn 1140
carytnwsnc cngtntgyaa yggnggnath atgacnccnc cnaarwsnac ngaraarccn 1200
ccnggnaarc aytrr 1215

<210> SEQ ID NO 9
<211> LENGTH: 26
<212> TYPE: DNA
<213> ORGANISM: synthetic construct

<400> SEQUENCE: 9
gaagagaatg tcaagacgaa gaagcc 26

<210> SEQ ID NO 10
<211> LENGTH: 26
<212> TYPE: DNA
<213> ORGANISM: synthetic construct

<400> SEQUENCE: 10
gcttaaatca ggcaaaggtg aaggat 26

<210> SEQ ID NO 11
<211> LENGTH: 27
<212> TYPE: DNA
<213> ORGANISM: synthetic construct

<400> SEQUENCE: 11
ccatcctaat acgactcact atagggc 27

<210> SEQ ID NO 12
<211> LENGTH: 24
<212> TYPE: DNA
<213> ORGANISM: synthetic construct

<400> SEQUENCE: 12
cagttctacc caatcttggt gaat 24

<210> SEQ ID NO 13
<211> LENGTH: 25
<212> TYPE: DNA
<213> ORGANISM: synthetic construct

<400> SEQUENCE: 13
atttaagctg ggcatgttca cagga 25

<210> SEQ ID NO 14
<211> LENGTH: 27
<212> TYPE: DNA
<213> ORGANISM: synthetic construct

<400> SEQUENCE: 14
gtcttcagct tcactggact cacactt 27

<210> SEQ ID NO 15
<211> LENGTH: 20
<212> TYPE: PRT
<213> ORGANISM: Human

-continued

<400> SEQUENCE: 15

Gly Gln Leu Ser Pro Val Cys Asn Gly Gly Ile Met Thr Pro Pro Lys
 1               5                  10                  15

Ser Thr Glu Lys
            20

<210> SEQ ID NO 16
<211> LENGTH: 21
<212> TYPE: PRT
<213> ORGANISM: Human

<400> SEQUENCE: 16

Ala Lys Gln Gln Pro Gln Pro Ser Gln Thr Glu Ser Pro Gln Glu Ala
 1               5                  10                  15

Gln Ile Ile Gln Ala
            20

<210> SEQ ID NO 17
<211> LENGTH: 1212
<212> TYPE: RNA
<213> ORGANISM: Mouse

<400> SEQUENCE: 17
augucccguc guucccgucu gcaggcuaaa cagcacgcuc agccgaacca gccggacucc      60
ccgcaggaaa cccagaucau ccaggcuaaa aaacguaaaa ccgcucagga cguuaaaaaa     120
cguaaagaag aaaucaccaa aaaacaccag uacgaaaucc guaacugcug gccgccgguu     180
cuguccggug guaucccccc gugcaucauc aucgaaaccc cgcacaaaga aaucgguacc     240
uccgacuucu cccguuucac caacuaccgu ucaaaaaacc uguucaucaa cccgucccg      300 cugccggacc uguccugggc uugcucccag gaaguuuggc agaacaugcu gcagaaagaa     360
aaccguuacg uucacgacaa acacuuccag guucugcacu ccgaccugga accgcagaug     420
cguuccaucc ugcuggacug gcugcuggaa guuugcgaag uuuacacccu gcaccgugaa     480
accuucuacc uggcucagga cuucuucgac cguucaugc ugaccagaa agacguuaac      540 aaaaacaugc ugcagcugau cgguaucacc ucccuguuca ucgcuuccaa acuggaagaa     600
aucuacgcuc cgaaacugca ggaauucgcu uacguuaccg acggugcuug ucccgaaguu     660
gacauccuga aaauggaacu gaacauccug aaagcucuga auggg aacu gugcccgguu     720 accguuaucu ccuggcugaa ccuguccug cagguugacg cuguuaaaga cguuccgaaa      780
guucugcugc cgcaguacuc ccaggaaaacc uucauccaga ucgcucagcu gcuggaccug     840
ugcauccugg cuaucgacuc ccuggaauuc caguaccgua ccuggcugc ugcugcucg       900 ugccacuuca ccuccaucga aguuguuaaa aaagcuuccg gucuggaaug ggacgacauc     960
uccgaaugcg uugacuggau gguuccguuc guuuccguug uuaaauccgu uuccccgguu    1020
aaacugaaaa ccuucaaaaa aaucccgaug gaagaccguc acaacaucca gacccacacc    1080
aacuaccugg cucugcugaa cgaaguuaac uacguuaaca ucuaccguaa agguggucag    1140
cuguccccgg uuugcaacgg ugguaucaug accccgccga aaccaccga aaaccgccg      1200 gguaaacacu ga                                                        1212

<210> SEQ ID NO 18
<211> LENGTH: 1212
<212> TYPE: DNA
<213> ORGANISM: Mouse

<400> SEQUENCE: 18

-continued

```
atgwsnmgnm gnwsnmgnyt ncargcnaar carcaygcnc arccnaayca rccngaywsn     60
ccncargara cncarathat hcargcnaar aarmgnaara cngcncarga ygtnaaraar    120
mgnaargarg arathacnaa raarcaycar taygarathm gnaaytgytg gccnccngtn    180
ytnwsnggng gnathwsncc ntgyathath athgaracnc cncayaarga rathggnacn    240
wsngayttyw snmgnttyac naaytaymgn ttyaaraayy tnttyathaa yccnwsnccn    300
ytnccngayy tnwsntgggc ntgywsncar gargtntggc araayatgyt ncaraargar    360
aaymgntayg tncaygayaa rcayttycar gtnytncayw sngayytnga rccncaratg    420
mgnwsnathy tnytngaytg gytnytngar gtntgygarg tntayacnyt ncaymgngar    480
acnttytayy tngcncarga yttyttygay mgnttyatgy tnacncaraa rgaygtnaay    540
aaraayatgy tncarytnat hggnathacn wsnytnttya thgcnwsnaa rytngargar    600
athtaygcnc cnaarytnca rgarttygcn taygtnacng ayggngcntg ywsngargtn    660
gayathytna aratggaryt naayathytn aargcnytna artgggaryt ntgyccngtn    720
acngtnathw sntggytnaa yytnttyytn cargtngayg cngtnaarga ygtnccnaar    780
gtnytnytnc cncartayws ncargaracn ttyathcara thgcncaryt nytngayytn    840
tgyathytng cnathgayws nytngartty cartaymgna thytngcngc ngcngcnytn    900
tgycayttya cnwsnathga rgtngtnaar aargcnwsng gnytngartg ggaygayath    960
wsngartgyg tngaytggat ggtnccntty gtnwsngtng tnaarwsngt nwsnccngtn   1020
aarytnaara cnttyaaraa rathccnatg gargaymgnc ayaayathca racncayacn   1080
aaytayytng cnytnytnaa ygargtnaay taygtnaaya thtaymgnaa rggnggncar   1140
ytnwsnccng tntgyaaygg nggnathatg acnccnccna arwsnacnga raarccnccn   1200
ggnaarcayt rr                                                       1212
```